United States Patent
Jebrail et al.

(10) Patent No.: US 12,239,988 B2
(45) Date of Patent: *Mar. 4, 2025

(54) AIR-MATRIX DIGITAL MICROFLUIDICS APPARATUSES AND METHODS FOR LIMITING EVAPORATION AND SURFACE FOULING

(71) Applicant: mirOculus Inc., San Francisco, CA (US)

(72) Inventors: Mais J. Jebrail, Toronto (CA); Irena Barbulovic-Nad, Toronto (CA); Lorenzo Gutierrez, North York (CA); Foteini Christodoulou, San Francisco, CA (US)

(73) Assignee: mirOculus Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/592,457

(22) Filed: Feb. 29, 2024

(65) Prior Publication Data

US 2024/0198343 A1 Jun. 20, 2024

Related U.S. Application Data

(63) Continuation of application No. 17/405,800, filed on Aug. 18, 2021, now Pat. No. 11,944,974, which is a
(Continued)

(51) Int. Cl.
| | |
|---|---|
| *B01L 3/00* | (2006.01) |
| *C12M 3/06* | (2006.01) |
| *G01N 27/447* | (2006.01) |

(52) U.S. Cl.
CPC ....... *B01L 3/502792* (2013.01); *C12M 23/16* (2013.01); *G01N 27/44791* (2013.01);
(Continued)

(58) Field of Classification Search
CPC ......... B01L 2200/027; B01L 2200/142; B01L 2300/042; B01L 2300/0874;
(Continued)

(56) References Cited

U.S. PATENT DOCUMENTS

| | | | |
|---|---|---|---|
| 4,469,863 | A | 9/1984 | Ts'o et al. |
| 4,492,322 | A | 1/1985 | Hieftje et al. |

(Continued)

FOREIGN PATENT DOCUMENTS

| | | |
|---|---|---|
| CA | 2470847 A1 | 7/2003 |
| CA | 2740113 A1 | 4/2010 |

(Continued)

OTHER PUBLICATIONS

Jebrail et al, "A Solvent Replenishment Solution for Managing Evaporation of Biochemical Reactions in Air-Matrix Digital Microfluidics Devices", Lab on a Chip, 15(1), pp. 151-158; Jan. 2015 (Year: 2015).*

(Continued)

*Primary Examiner* — Jennifer Wecker
(74) *Attorney, Agent, or Firm* — Shay Glenn LLP

(57) ABSTRACT

Air-matrix digital microfluidics (DMF) apparatuses and methods of using them to prevent or limit evaporation and surface fouling of the DMF apparatus. In particular, described herein are air-matrix DMF apparatuses and methods of using them in which a separate well that is accessible from the air gap of the DMF apparatus isolates a reaction droplet by including a cover to prevent evaporation. The cover may be a lid or cap, or it may be an oil or wax material within the well. The opening into the well and/or the well itself may include actuation electrodes to allow the droplet to be placed into, and in some cases removed from, the well. Also described herein are air-matrix DMF apparatuses and methods of using them including thermally controllable
(Continued)

regions with a wax material that may be used to selectively encapsulate a reaction droplet in the air gap of the apparatus.

20 Claims, 9 Drawing Sheets

Related U.S. Application Data continuation of application No. 16/523,876, filed on Jul. 26, 2019, now Pat. No. 11,097,276, which is a continuation of application No. 15/579,455, filed as application No. PCT/US2016/036015 on Jun. 6, 2016, now Pat. No. 10,464,067.

(60) Provisional application No. 62/171,756, filed on Jun. 5, 2015.

(52) U.S. Cl.
CPC ... *B01L 2200/027* (2013.01); *B01L 2200/142* (2013.01); *B01L 2300/042* (2013.01); *B01L 2300/0874* (2013.01); *B01L 2300/18* (2013.01); *B01L 2300/1822* (2013.01); *B01L 2400/0415* (2013.01); *B01L 2400/0427* (2013.01)

(58) Field of Classification Search
CPC ......... B01L 2300/18; B01L 2300/1822; B01L 2400/0415; B01L 2400/0427; B01L 3/502792; C12M 23/16; G01N 27/44791
See application file for complete search history.

(56) References Cited

U.S. PATENT DOCUMENTS

| | | |
|---|---|---|
| 4,569,575 A | 2/1986 | Le Pesant et al. |
| 4,636,785 A | 1/1987 | Le Pesant |
| 4,818,052 A | 4/1989 | Le Pesant et al. |
| 5,034,506 A | 7/1991 | Summerton et al. |
| 5,130,238 A | 7/1992 | Malek et al. |
| 5,216,141 A | 6/1993 | Benner |
| 5,235,033 A | 8/1993 | Summerton et al. |
| 5,270,185 A | 12/1993 | Margolskee |
| 5,386,023 A | 1/1995 | Sanghvi et al. |
| 5,399,491 A | 3/1995 | Kacian et al. |
| 5,409,818 A | 4/1995 | Davey et al. |
| 5,411,876 A | 5/1995 | Bloch et al. |
| 5,455,166 A | 10/1995 | Walker |
| 5,486,337 A | 1/1996 | Ohkawa |
| 5,602,240 A | 2/1997 | De Mesmaeker et al. |
| 5,637,684 A | 6/1997 | Cook et al. |
| 5,644,048 A | 7/1997 | Yau |
| 5,681,702 A | 10/1997 | Collins et al. |
| 5,705,365 A | 1/1998 | Ryder et al. |
| 5,710,029 A | 1/1998 | Ryder et al. |
| 5,806,515 A | 9/1998 | Bare et al. |
| 5,888,779 A | 3/1999 | Kacian et al. |
| 6,007,690 A | 12/1999 | Nelson et al. |
| 6,074,725 A | 6/2000 | Kennedy |
| 6,294,063 B1 | 9/2001 | Becker et al. |
| 6,352,838 B1 | 3/2002 | Krulevitch et al. |
| 6,353,149 B1 | 5/2002 | Stone |
| 6,401,552 B1 | 6/2002 | Elkins |
| 6,495,369 B1 | 12/2002 | Kerceo et al. |
| 6,565,727 B1 | 5/2003 | Shenderov |
| 6,596,988 B2 | 7/2003 | Corso et al. |
| 6,656,428 B1 | 12/2003 | Clark et al. |
| 6,723,985 B2 | 4/2004 | Schultz et al. |
| 6,773,566 B2 | 8/2004 | Shenderov |
| 6,787,111 B2 | 9/2004 | Roach et al. |
| 6,887,384 B1 | 5/2005 | Frechet et al. |
| 6,911,132 B2 | 6/2005 | Pamula et al. |
| 6,989,234 B2 | 1/2006 | Kolar et al. |
| 7,057,031 B2 | 6/2006 | Olejnik et al. |
| 7,147,763 B2 | 12/2006 | Elrod et al. |
| 7,163,612 B2 | 1/2007 | Sterling et al. |
| 7,214,302 B1 | 5/2007 | Reihs et al. |
| 7,323,345 B1 | 1/2008 | Stjernstrom |
| 7,328,979 B2 | 2/2008 | Decre et al. |
| 7,329,545 B2 | 2/2008 | Pamula et al. |
| 7,349,014 B2 | 3/2008 | Higashihara |
| 7,390,463 B2 | 6/2008 | He et al. |
| 7,391,020 B2 | 6/2008 | Bousse et al. |
| 7,439,014 B1 | 10/2008 | Pamula et al. |
| 7,445,926 B2 | 11/2008 | Mathies et al. |
| 7,531,120 B2 | 5/2009 | Van Rijn et al. |
| D599,832 S | 9/2009 | Chapin et al. |
| 7,713,456 B2 | 5/2010 | Dodd et al. |
| 7,727,723 B2 | 6/2010 | Pollack et al. |
| 7,745,207 B2 | 6/2010 | Jovanovich et al. |
| 7,763,471 B2 | 7/2010 | Pamula et al. |
| 7,815,871 B2 | 10/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,897,737 B2 | 3/2011 | Wu et al. |
| 7,901,947 B2 | 3/2011 | Pollack et al. |
| 7,919,330 B2 | 4/2011 | de Guzman et al. |
| 7,939,021 B2 | 5/2011 | Smith et al. |
| 7,998,436 B2 | 8/2011 | Pollack et al. |
| 8,007,739 B2 | 8/2011 | Pollack et al. |
| 8,041,463 B2 | 10/2011 | Pollack et al. |
| 8,053,239 B2 | 11/2011 | Wheeler et al. |
| 8,088,578 B2 | 1/2012 | Hua et al. |
| 8,093,062 B2 | 1/2012 | Winger |
| 8,137,917 B2 | 3/2012 | Pollack et al. |
| 8,187,864 B2 | 5/2012 | Wheeler et al. |
| 8,190,371 B2 | 5/2012 | Allawi et al. |
| 8,202,686 B2 | 6/2012 | Pamula et al. |
| 8,202,736 B2 | 6/2012 | Mousa et al. |
| 8,208,146 B2 | 6/2012 | Srinivasan et al. |
| 8,268,246 B2 | 9/2012 | Srinivasan et al. |
| 8,304,253 B2 | 11/2012 | Yi et al. |
| 8,317,990 B2 | 11/2012 | Pamula et al. |
| 8,349,276 B2 | 1/2013 | Pamula et al. |
| 8,364,315 B2 | 1/2013 | Sturmer et al. |
| 8,367,370 B2 | 2/2013 | Wheeler et al. |
| 8,389,297 B2 | 3/2013 | Pamula et al. |
| 8,394,641 B2 | 3/2013 | Winger |
| 8,399,222 B2 | 3/2013 | Siva et al. |
| 8,426,213 B2 | 4/2013 | Eckhardt et al. |
| 8,440,392 B2 | 5/2013 | Pamula et al. |
| 8,454,905 B2 | 6/2013 | Pope et al. |
| 8,460,528 B2 | 6/2013 | Pollack et al. |
| 8,470,153 B2 | 6/2013 | Feiglin et al. |
| 8,470,606 B2 | 6/2013 | Srinivasan et al. |
| 8,481,125 B2 | 7/2013 | Yi et al. |
| 8,492,168 B2 | 7/2013 | Srinivasan et al. |
| 8,562,807 B2 | 10/2013 | Srinivasan et al. |
| 8,591,830 B2 | 11/2013 | Sudarsan et al. |
| 8,592,217 B2 | 11/2013 | Eckhardt |
| 8,613,889 B2 | 12/2013 | Pollack et al. |
| 8,637,317 B2 | 1/2014 | Pamula et al. |
| 8,637,324 B2 | 1/2014 | Pollack et al. |
| 8,653,832 B2 | 2/2014 | Hadwen et al. |
| 8,658,111 B2 | 2/2014 | Srinivasan et al. |
| 8,685,344 B2 | 4/2014 | Sudarsan et al. |
| 8,685,754 B2 | 4/2014 | Pollack et al. |
| 8,702,938 B2 | 4/2014 | Srinivasan et al. |
| 8,716,015 B2 | 5/2014 | Pollack et al. |
| 8,809,068 B2 | 8/2014 | Sista et al. |
| 8,821,705 B2 | 9/2014 | Bjornson et al. |
| 8,845,872 B2 | 9/2014 | Pollack et al. |
| 8,846,414 B2 | 9/2014 | Sista et al. |
| 8,852,952 B2 | 10/2014 | Pollack et al. |
| 8,872,527 B2 | 10/2014 | Sturmer et al. |
| 8,877,512 B2 | 11/2014 | Srinivasan et al. |
| 8,888,969 B2 | 11/2014 | Soleymani et al. |
| 8,901,043 B2 | 12/2014 | Eckhardt et al. |
| 8,926,065 B2 | 1/2015 | Winger |
| 8,927,296 B2 | 1/2015 | Sista et al. |
| 8,936,708 B2 | 1/2015 | Feiglin et al. |

(56) References Cited

U.S. PATENT DOCUMENTS

| | | |
|---|---|---|
| 8,951,732 B2 | 2/2015 | Pollack et al. |
| 8,980,198 B2 | 3/2015 | Srinivasan et al. |
| 9,005,544 B2 | 4/2015 | Van Dam et al. |
| 9,011,662 B2 | 4/2015 | Wang et al. |
| 9,039,973 B2 | 5/2015 | Watson et al. |
| 9,046,514 B2 | 6/2015 | Sista et al. |
| 9,091,649 B2 | 7/2015 | Pollack et al. |
| 9,140,635 B2 | 9/2015 | Graham et al. |
| 9,188,615 B2 | 11/2015 | Sturmer et al. |
| 9,223,317 B2 | 12/2015 | Winger |
| 9,238,222 B2 | 1/2016 | Delattre et al. |
| 9,248,450 B2 | 2/2016 | Bauer |
| 9,377,439 B2 | 6/2016 | Lee et al. |
| 9,435,765 B2 | 9/2016 | Reimitz et al. |
| 9,446,404 B2 | 9/2016 | Bauer et al. |
| 9,476,811 B2 | 10/2016 | Mudrik et al. |
| 9,476,856 B2 | 10/2016 | Pamula et al. |
| 9,513,253 B2 | 12/2016 | Winger |
| 9,517,469 B2 | 12/2016 | Shenderov et al. |
| 9,594,056 B2 | 3/2017 | Fobel et al. |
| 9,851,365 B2 | 12/2017 | Mousa et al. |
| 9,975,117 B2 | 5/2018 | Lee et al. |
| 10,232,374 B2 | 3/2019 | Jebrail et al. |
| 10,464,067 B2 | 11/2019 | Jebrail et al. |
| 10,596,572 B2 | 3/2020 | Hong et al. |
| 10,695,762 B2 | 6/2020 | Jebrail et al. |
| 11,097,276 B2 | 8/2021 | Jebrail et al. |
| 11,253,860 B2 | 2/2022 | Jebrail et al. |
| 11,298,700 B2 | 4/2022 | Hong et al. |
| 11,311,882 B2 | 4/2022 | Soto-Moreno et al. |
| 11,413,617 B2 | 8/2022 | Jebrail et al. |
| 11,471,888 B2 | 10/2022 | Jebrail et al. |
| 11,524,298 B2 | 12/2022 | Soto-Moreno et al. |
| 11,623,219 B2 | 4/2023 | Jebrail et al. |
| 11,738,345 B2 | 8/2023 | Soto-Moreno et al. |
| 11,772,093 B2 | 10/2023 | Jebrail et al. |
| 11,833,516 B2 | 12/2023 | Jebrail et al. |
| 11,857,961 B2 | 1/2024 | Jebrail et al. |
| 11,857,969 B2 | 1/2024 | Jebrail et al. |
| 11,890,617 B2 | 2/2024 | Jebrail et al. |
| 11,944,974 B2 | 4/2024 | Jebrail et al. |
| 2002/0150683 A1 | 10/2002 | Troian et al. |
| 2003/0017551 A1 | 1/2003 | Parthasarathy et al. |
| 2003/0136451 A1 | 7/2003 | Beebe et al. |
| 2003/0194716 A1 | 10/2003 | Knoll |
| 2004/0171169 A1 | 9/2004 | Kallury et al. |
| 2004/0211659 A1 | 10/2004 | Velev |
| 2005/0115836 A1 | 6/2005 | Reihs |
| 2005/0133370 A1 | 6/2005 | Park et al. |
| 2005/0148091 A1 | 7/2005 | Kitaguchi et al. |
| 2005/0191759 A1 | 9/2005 | Pedersen Bjergaard et al. |
| 2005/0220675 A1 | 10/2005 | Reed et al. |
| 2006/0091015 A1 | 5/2006 | Lau |
| 2006/0132542 A1 | 6/2006 | Bruker et al. |
| 2006/0231398 A1 | 10/2006 | Sarrut et al. |
| 2006/0272942 A1 | 12/2006 | Sirringhaus |
| 2007/0023292 A1 | 2/2007 | Kim et al. |
| 2007/0095407 A1 | 5/2007 | Chen et al. |
| 2007/0138664 A1 | 6/2007 | Chen et al. |
| 2007/0148763 A1 | 6/2007 | Huh et al. |
| 2007/0258864 A1 | 11/2007 | Braymer et al. |
| 2007/0269825 A1 | 11/2007 | Wang et al. |
| 2008/0110753 A1 | 5/2008 | Fourrier et al. |
| 2008/0131904 A1 | 6/2008 | Parce et al. |
| 2008/0156983 A1 | 7/2008 | Fourrier et al. |
| 2008/0169197 A1 | 7/2008 | McRuer et al. |
| 2008/0185339 A1 | 8/2008 | Delapierre et al. |
| 2008/0210558 A1 | 9/2008 | Sauter-Starace et al. |
| 2008/0211849 A1 | 9/2008 | Pierik et al. |
| 2008/0241831 A1 | 10/2008 | Fan et al. |
| 2008/0293051 A1 | 11/2008 | Levy et al. |
| 2009/0017197 A1 | 1/2009 | Zhang et al. |
| 2009/0017453 A1 | 1/2009 | Maples et al. |
| 2009/0051736 A1 | 2/2009 | Sugahara |
| 2009/0124721 A1 | 5/2009 | Chen et al. |
| 2009/0207206 A1 | 8/2009 | Harada |
| 2009/0286297 A1 | 11/2009 | Pihl et al. |
| 2010/0015614 A1 | 1/2010 | Beer et al. |
| 2010/0022414 A1 | 1/2010 | Link et al. |
| 2010/0025250 A1 | 2/2010 | Pamula et al. |
| 2010/0032293 A1 | 2/2010 | Pollack et al. |
| 2010/0048410 A1 | 2/2010 | Shenderov et al. |
| 2010/0087012 A1 | 4/2010 | Shenderov |
| 2010/0120130 A1 | 5/2010 | Srinivasan et al. |
| 2010/0130369 A1 | 5/2010 | Shenderov et al. |
| 2010/0136544 A1 | 6/2010 | Agresti et al. |
| 2010/0206094 A1 | 8/2010 | Shenderov |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0270156 A1 | 10/2010 | Srinivasan et al. |
| 2010/0288368 A1 | 11/2010 | Beebe et al. |
| 2010/0311599 A1 | 12/2010 | Wheeler et al. |
| 2011/0024793 A1 | 2/2011 | Jeon |
| 2011/0076685 A1 | 3/2011 | Moeller et al. |
| 2011/0097763 A1 | 4/2011 | Pollack et al. |
| 2011/0104725 A1 | 5/2011 | Pamula et al. |
| 2011/0104747 A1 | 5/2011 | Pollack et al. |
| 2011/0107822 A1 | 5/2011 | Bunner et al. |
| 2011/0147216 A1 | 6/2011 | Fan et al. |
| 2011/0220501 A1 | 9/2011 | Witkowski et al. |
| 2011/0240471 A1 | 10/2011 | Wheeler et al. |
| 2011/0247934 A1 | 10/2011 | Wang et al. |
| 2011/0293851 A1 | 12/2011 | Bollström et al. |
| 2011/0303542 A1 | 12/2011 | Srinivasan et al. |
| 2011/0311980 A1 | 12/2011 | Pollack et al. |
| 2012/0000777 A1 | 1/2012 | Garrell et al. |
| 2012/0045748 A1 | 2/2012 | Willson et al. |
| 2012/0045768 A1 | 2/2012 | Arunachalam et al. |
| 2012/0085645 A1* | 4/2012 | Mousa ............... G01N 33/74 204/601 |
| 2012/0149018 A1 | 6/2012 | Dahlberg et al. |
| 2012/0190027 A1 | 7/2012 | Loeffert et al. |
| 2012/0190589 A1 | 7/2012 | Anderson et al. |
| 2012/0208705 A1 | 8/2012 | Steemers et al. |
| 2012/0208724 A1 | 8/2012 | Steemers et al. |
| 2012/0259233 A1 | 10/2012 | Chan et al. |
| 2012/0261264 A1 | 10/2012 | Srinivasan et al. |
| 2012/0289581 A1 | 11/2012 | Chang et al. |
| 2012/0325665 A1 | 12/2012 | Chiou et al. |
| 2013/0017544 A1 | 1/2013 | Eckhardt et al. |
| 2013/0018611 A1 | 1/2013 | Sturmer |
| 2013/0062205 A1 | 3/2013 | Hadwen et al. |
| 2013/0068622 A1 | 3/2013 | Schertzer et al. |
| 2013/0105318 A1 | 5/2013 | Bhattacharya et al. |
| 2013/0123979 A1 | 5/2013 | Elliot et al. |
| 2013/0157259 A1 | 6/2013 | Choi et al. |
| 2013/0168250 A1 | 7/2013 | Fogleman et al. |
| 2013/0171546 A1 | 7/2013 | White et al. |
| 2013/0177915 A1 | 7/2013 | Too et al. |
| 2013/0203606 A1 | 8/2013 | Pollack et al. |
| 2013/0215492 A1 | 8/2013 | Steckl et al. |
| 2013/0217113 A1 | 8/2013 | Srinivasan et al. |
| 2013/0225450 A1 | 8/2013 | Pollack et al. |
| 2013/0236377 A1 | 9/2013 | Kim et al. |
| 2013/0270114 A1 | 10/2013 | Feiglin |
| 2013/0284956 A1 | 10/2013 | Kwon |
| 2013/0288254 A1 | 10/2013 | Pollack et al. |
| 2013/0293246 A1 | 11/2013 | Pollack et al. |
| 2013/0306480 A1 | 11/2013 | Chang et al. |
| 2014/0005066 A1 | 1/2014 | Boles et al. |
| 2014/0054174 A1 | 2/2014 | Wang |
| 2014/0124037 A1 | 5/2014 | Foley |
| 2014/0141409 A1 | 5/2014 | Foley et al. |
| 2014/0161686 A1 | 6/2014 | Bort et al. |
| 2014/0174926 A1 | 6/2014 | Bort et al. |
| 2014/0179539 A1 | 6/2014 | Ohman et al. |
| 2014/0194305 A1 | 7/2014 | Kayyem et al. |
| 2014/0216559 A1 | 8/2014 | Foley |
| 2014/0272965 A1 | 9/2014 | Handique et al. |
| 2014/0273100 A1 | 9/2014 | Saito et al. |
| 2014/0335069 A1 | 11/2014 | Graham et al. |
| 2014/0353157 A1 | 12/2014 | Hoffmeyer et al. |
| 2015/0001078 A1 | 1/2015 | Feiglin |

(56) References Cited

U.S. PATENT DOCUMENTS

| | | |
|---|---|---|
| 2015/0008123 A1 | 1/2015 | Cheng et al. |
| 2015/0021182 A1 | 1/2015 | Rival et al. |
| 2015/0075986 A1 | 3/2015 | Cyril et al. |
| 2015/0111237 A1 | 4/2015 | Graham et al. |
| 2015/0144489 A1 | 5/2015 | Hoffmeyer et al. |
| 2015/0148549 A1 | 5/2015 | Van dam et al. |
| 2015/0198604 A1 | 6/2015 | Ermantraut et al. |
| 2015/0205272 A1 | 7/2015 | Yi et al. |
| 2015/0212043 A1 | 7/2015 | Pollack |
| 2015/0238959 A1 | 8/2015 | Prakash et al. |
| 2015/0258520 A1 | 9/2015 | Griffiths et al. |
| 2015/0267242 A1 | 9/2015 | Foegeding et al. |
| 2015/0322272 A1 | 11/2015 | Pokroy et al. |
| 2016/0068901 A1 | 3/2016 | Eckhardt et al. |
| 2016/0108432 A1 | 4/2016 | Punnamaraju et al. |
| 2016/0108433 A1 | 4/2016 | Fair et al. |
| 2016/0116438 A1 | 4/2016 | Pamula et al. |
| 2016/0129437 A1 | 5/2016 | Kayyem et al. |
| 2016/0161343 A1 | 6/2016 | Smith et al. |
| 2016/0175859 A1 | 6/2016 | Yi et al. |
| 2016/0199832 A1 | 7/2016 | Jamshidi et al. |
| 2016/0273032 A1 | 9/2016 | Esfandyarpour |
| 2016/0298173 A1 | 10/2016 | Wang et al. |
| 2016/0319354 A1 | 11/2016 | Tocigl et al. |
| 2016/0370317 A9 | 12/2016 | Sudarsan et al. |
| 2017/0184546 A1 | 6/2017 | Fobel et al. |
| 2017/0315090 A1 | 11/2017 | Wheeler et al. |
| 2017/0354973 A1 | 12/2017 | Sustarich et al. |
| 2018/0095067 A1 | 4/2018 | Huff et al. |
| 2018/0099275 A1 | 4/2018 | Wu et al. |
| 2018/0120335 A1 | 5/2018 | Mousa et al. |
| 2018/0193831 A1 | 7/2018 | Hopper |
| 2018/0250672 A1 | 9/2018 | Jamshidi et al. |
| 2019/0210026 A1 | 7/2019 | Jebrail et al. |
| 2019/0374950 A1 | 12/2019 | Fobel et al. |
| 2020/0261913 A1 | 8/2020 | Williams et al. |
| 2021/0069714 A1 | 3/2021 | Jebrail et al. |
| 2022/0161216 A1 | 5/2022 | Cervantes et al. |
| 2022/0219172 A1 | 7/2022 | Soto-Moreno et al. |
| 2022/0250078 A1 | 8/2022 | Soto-Moreno et al. |
| 2022/0395835 A1 | 12/2022 | Soto-Moreno et al. |
| 2022/0401957 A1 | 12/2022 | Jebrail et al. |
| 2023/0219094 A1 | 7/2023 | Soto-Moreno et al. |
| 2023/0249185 A1 | 8/2023 | Jebrail et al. |
| 2023/0398541 A1 | 12/2023 | Soto-Moreno et al. |
| 2024/0100524 A1 | 3/2024 | Jebrail et al. |

FOREIGN PATENT DOCUMENTS

| | | |
|---|---|---|
| CA | 2881783 A1 | 2/2014 |
| CN | 1668527 A | 9/2005 |
| CN | 101609063 A | 12/2009 |
| CN | 102549804 A | 7/2012 |
| CN | 102719526 A | 10/2012 |
| CN | 102740976 A | 10/2012 |
| CN | 102836653 A | 12/2012 |
| CN | 103014148 A | 4/2013 |
| CN | 103170383 A | 6/2013 |
| CN | 103502386 A | 1/2014 |
| CN | 103946712 A | 7/2014 |
| CN | 104144748 A | 11/2014 |
| CN | 104321141 A | 1/2015 |
| CN | 104995261 A | 10/2015 |
| CN | 105764490 A | 7/2016 |
| CN | 105849032 A | 8/2016 |
| DE | 19949735 A1 | 5/2001 |
| EP | 2111554 B1 | 5/2013 |
| GB | 2533952 A | 7/2016 |
| JP | 2002321449 A | 11/2002 |
| JP | 2006220606 A | 8/2006 |
| JP | 2010500596 A | 1/2010 |
| JP | 2010098133 A | 4/2010 |
| JP | 2010515877 A | 5/2010 |
| JP | 2010180222 A | 8/2010 |
| JP | 2012525687 A | 10/2012 |
| JP | 2015529815 A | 10/2015 |
| WO | WO2000/067907 A2 | 11/2000 |
| WO | WO2001/025137 A1 | 4/2001 |
| WO | WO2003/045556 A2 | 6/2003 |
| WO | WO2004/055260 A1 | 7/2004 |
| WO | WO2004/074169 A1 | 9/2004 |
| WO | WO2005/068993 A1 | 7/2005 |
| WO | WO2005/118129 A1 | 12/2005 |
| WO | WO2006/000828 A2 | 1/2006 |
| WO | WO2006/102309 A2 | 9/2006 |
| WO | WO2007/120240 A2 | 10/2007 |
| WO | WO2007/123908 A2 | 11/2007 |
| WO | WO2007/130294 A2 | 11/2007 |
| WO | WO2007/136386 A2 | 11/2007 |
| WO | WO2008/066828 A2 | 6/2008 |
| WO | WO2009/026339 A2 | 2/2009 |
| WO | WO2009/052348 A2 | 4/2009 |
| WO | WO2009/111723 A1 | 9/2009 |
| WO | WO2009/111769 A2 | 9/2009 |
| WO | WO2009/140671 A2 | 11/2009 |
| WO | WO2010/003188 A1 | 1/2010 |
| WO | WO2010/006166 A2 | 1/2010 |
| WO | WO2010/027894 A2 | 3/2010 |
| WO | WO2010/042637 A2 | 4/2010 |
| WO | WO2010/069977 A1 | 6/2010 |
| WO | WO2010/091334 A2 | 8/2010 |
| WO | WO2010/111265 A1 | 9/2010 |
| WO | WO2011/002957 A2 | 1/2011 |
| WO | WO2011/062557 A1 | 5/2011 |
| WO | WO2012/061832 A1 | 5/2012 |
| WO | WO2012/172172 A1 | 12/2012 |
| WO | WO2013/006312 A2 | 1/2013 |
| WO | WO2013/040562 A2 | 3/2013 |
| WO | WO2013/090889 A1 | 6/2013 |
| WO | WO2013/096839 A1 | 6/2013 |
| WO | WO2013/116039 A1 | 8/2013 |
| WO | WO2013/176767 A1 | 11/2013 |
| WO | WO2014/078100 A1 | 5/2014 |
| WO | WO2014/083622 A1 | 6/2014 |
| WO | WO2014/100473 A1 | 6/2014 |
| WO | WO2014/106167 A1 | 7/2014 |
| WO | WO2014/108185 A1 | 7/2014 |
| WO | WO2014/183118 A1 | 11/2014 |
| WO | WO2015/023745 A1 | 2/2015 |
| WO | WO2015/077737 A1 | 5/2015 |
| WO | WO2015/172255 A1 | 11/2015 |
| WO | WO2015/172256 A1 | 11/2015 |
| WO | WO2016/006184 A1 | 1/2016 |
| WO | WO2016/094589 A1 | 6/2016 |
| WO | WO2016/128544 A1 | 8/2016 |
| WO | WO2016/182814 A2 | 11/2016 |
| WO | WO2016/197013 A1 | 12/2016 |
| WO | WO2017/094021 A1 | 6/2017 |

OTHER PUBLICATIONS

Abdelgawad et al., All-terrain droplet actuation, Lab on a Chip, 8(5), pp. 672-677, May 2008.

Abdelgawad et al.; Low-cost, rapid-prototyping of digital microfluidics devices, Microfluidics and Nanofluidics, 4, pp. 349-355, Apr. 2008.

Abdelgawad et al.; Rapid prototyping in copper substrates for digital microfluidics, Adv. Mater., 19(1), pp. 133-137; Jan. 2007.

Abdelgawad et al.; Hybrid microfluidics: a digital-to-channel interface for in-line sample processing and chemical separations, Lab on a Chip, 9(8), pp. 1046-1051, Apr. 2009.

Abdelgawad; Digital Microfluidics for Integration of Lab-on-a-Chip Devices (Doctoral dissertation); University of Toronto; © 2009.

Albrecht et al.; Laboratory testing of gonadal steroids in children; Pediatric Endocrinology Reviews; 5(suppl 1); pp. 599-607; Oct. 2007.

Analog Devices; 24-bit Capicitance-to-Digital converter with temperature sensor, AD7745/AD7746; Analog Devices; Norwood, MA; 28 pages; (the year of publication is sufficiently earlier than the effective U.S. filing date and any foreign priority date so that the particular month of publication is not in issue) 2005.

(56) References Cited

OTHER PUBLICATIONS

Analog Devices; Extending the capacitive input range of AD7745/AD7746 Capicitance-to-Digital converter; Analog Devices; Norwood, MA; 5 pages; (the year of publication is sufficiently earlier than the effective U.S. filing date and any foreign priority date so that the particular month of publication is not in issue) 2009.
Ankarberg-Lindren et al.; A purification step prior to commercial sensitive immunoassay is necessary to achieve clinical usefulness when quantifying serum 17 ?-estradiol in prepubertal children. Eur J Endocrinol, 158, pp. 117-124, Jan. 2008.
Armstrong et al.; A study of plasma free amino acid levels. II. Normal values for children and adults, Metabolism, 22(4), pp. 561-569, Apr. 1973.
Asiello et al.; Miniaturized isothermal nucleic acid amplification, a review; Lab Chip; 11(8); pp. 1420-1430; Apr. 2011.
Au et al., Integrated microbioreactor for culture and analysis of bacteria, algae and yeast, Biomedical Microdevices, 13(1), pp. 41-50, Feb. 2011.
Au et al.; A new angle on pluronic additives: Advancing droplets and understanding in digital microfluidics; Langmuir; 27; pp. 8586-8594; Jun. 2011.
Banatvala et al., Rubella, The Lancet, 363(9415), pp. 1127-1137, Apr. 2004.
Banér et al.; Signal amplification of padlock probes by rolling circle replication; Nuc. Acids Res.; 26(22); pp. 5073-5078; Nov. 1998.
Barany; Genetic disease detection and DNA amplification using cloned thermostable ligase; PNAS; 88(1); pp. 189-193; Jan. 1991.
Barbulovic-Nad et al., A microfluidic platform for complete mammalian cell culture, Lab on a Chip, 10(12), pp. 1536-1542; Jun. 2010.
Barbulovic-Nad et al.; Digital microfluidics for cell-based assays, Lab Chip, 8(4), pp. 519-526; Apr. 2008.
Baxendale et al. ; Multistep synthesis using modular flow reactors: bestmann-ohira reagent for the formation of alkynes and triazoles; Angewandle Chemie International Edition; 48(22); pp. 4017-4021; May 2009.
Beattie et al.; Endogenous sex hormones, breast cancer risk, and tamoxifen response: an ancillary study in the NSABP Breast Cancer Prevention Trial P-1, J Natl Cancer Inst, 98(2), pp. 110-115, Jan. 2006.
Beaucage et al., The Functionalization of Oligonucleotides via Phosphoramidite Derivatives, Tetrahedron, 49(10), pp. 1925-1963, Mar. 1993.
Belanger et al.; Omental and subcutaneous adipose tissue steroid levels in obese men. Steroids, 71(8), pp. 674-682, Aug. 2006.
Bergkvist et al., Improved chip design for integrated solid-phase microextraction in on-line proteomic sample preparation, Proteomics, 2(4), pp. 422-429, Apr. 2002.
Bi et al.; Dumbbell probe-mediated cascade isothermal amplification. A novel strategy for label-free detection of microRNAs and its application to real sample assay; Analytica Chimica Acta; 760; pp. 69-74; Jan. 2013.
Blankenstein et al.; Intratumoral levels of estrogens in breast cancer. J Steroid Biochem Mol Biol, 69(1-6), pp. 293-297, Apr.-Jun. 1999.
Bodamer et al.; Expanded newborn screening in Europe, Journal of Inherited Metabolic Disease, 30(4), pp. 439-444, Aug. 2007.
Bohlen et al.; Fluorometric assay of proteins in the nanogram range, Archives of Biochemistry and Biophysics, 155(1), pp. 213-220, Mar. 1973.
Boles et al.;Droplet-Based Pyrosequencing Using Digital Microfluidics; Analytical Chemistry; 83(22); pp. 8439-8447; Oct. 14, 2011.
Bollström et al.; A Multilayer Coated Fiber-Based Substrate Suitable for Printed Functionality; Organic Electronics; 10(5); pp. 1020-1023; Aug. 2009.
Bonneil et al., Integration of solid-phase extraction membranes for sample multiplexing: Application to rapid protein identification from gel-isolated protein extracts, Electrophoresis, 23(20), pp. 3589-3598, Oct. 2002.
Brassard et al.; Water-oil core-shell droplets for electrowetting-based digital microfluidic devices; Lab Chip; 8(8); pp. 1342-1349; Aug. 2008.
Brill et al., Synthesis of oligodeoxynucleoside phosphorodithioates via thioamidites, J. Am. Chem. Soc., 111(6), pp. 2321-2322, Mar. 1989.
Brivio et al.; Integrated microfluidic system enabling (bio)chemical reactions with on-line MALDI-TOF mass spectrometry, Anal. Chem., 74(16), pp. 3972-3976, Aug. 2002.
Burstein; Aromatase inhibitor-associated arthralgia syndrome. Breast, 16(3), pp. 223-234, Jun. 2007.
Carlsson et al., Screening for genetic mutations, Nature, 380(6571), pp. 207, Mar. 1996.
Chace et al.; A biochemical perspective on the use of tandem mass spectrometry for newborn screening and clinical testing, Clinical Biochemistry, 38(4), pp. 296-309; Apr. 2005.
Chace et al.; Rapid diagnosis of maple syrup urine disease in blood spots from newborns by tandem mass spectrometry, Clinical Chemistry, 41(1), pp. 62-68, Jan. 1995.
Chace et al.; Rapid diagnosis of phenylketonuria by quantitative analysis for phenylalanine and tyrosine in neonatal blood spots by tandem mass spectrometry, Clinical Chemistry, 39(1), pp. 66-71; Jan. 1993.
Chace et al.; Use of tandem mass spectrometry for multianalyte screening of dried blood specimens from newborns, Clinical Chemistry, 49(11), pp. 1797-1817, Nov. 2003.
Chace; Mass spectrometry in newborn and metabolic screening: historical perspective and future directions, Journal of Mass Spectrometry, 44(2), pp. 163-170, Feb. 2009.
Chang et al.; Integrated polymerase chain reaction chips utilizing digital microfluidics; Biomedical Microdevices; 8(3); pp. 215-225; Sep. 2006.
Chatterjee et al.; Droplet-based microfluidics with nonaqueous solvents and solutions, Lab Chip, 6(2), pp. 199-206, Feb. 2006.
Chen et al.; Selective Wettability Assisted Nanoliter Sample Generation via Electrowetting-Based Transportation; Proceedings of the 5th International Conference on Nanochannels, Microchannels and Minichannels (ICNMM); Puebla, Mexico; Paper No. ICNMM2007-30184; pp. 147-153; Jun. 18-20, 2007.
Chen et al.; The chemistrode: a droplet-based microfluidic device for stimulation and recording with high temporal, spatial, and chemical resolution; Proceedings of the National Academy of Sciences; 105(44); pp. 16843-16848; Nov. 2004.
Cheng et al., Paper-Based ELISA, Angewandte Chemie, 49(28), pp. 4771-4774, Jun. 2010.
Cheng et al.; Highly Sensitive Determination of microRNA Using Target-Primed and Branched Rolling-Circle Amplification; Angew. Chem.; 121(18); pp. 3318-3322; Apr. 2009.
Chetrite et al.; Estradiol inhibits the estrone sulfatase activity in normal and cancerous human breast tissues. Journal of Steroid Biochemistry and Molecular Biology, 104(3-5), pp. 289-292, May 2007.
Cho et al.; Creating, transporting, cutting, and merging liquid droplets by electrowetting-based actuation for digital microfluidic circuits, J. MEMS 2003, 12(1), pp. 70-80, Feb. 2003.
Choi et al., Automated digital microfluidic platform for magnetic-particle-based immunoassays with optimization by design of experiments, Anal. Chem., 85(20), pp. 9638-9646; Oct. 2013.
Choi et al., Digital Microfluidics, Annu. Rev. Anal. Chem., 5, pp. 413-440, (Epub) Apr. 2012.
Christiansen; Hormone Replacement Therapy and Osteoporosis; Maturitas, 23, Suppl. pp. S71-S76, May 1996.
Chuang et al.; Direct Handwriting Manipulation of Droplets by Self-Aligned Mirror-EWOO Across a Dielectric Sheet; 19th IEEE International Conf. on Micro Electro Mechanical Systems (MEMS); Instanbul, Turkey; pp. 538-541; Jan. 22-26, 2006.
Cipriano et al.; The cost-effectiveness of expanding newborn screening for up to 21 inherited metabolic disorders using tandem mass spectrometry: results from a decision-analytic model, Value in Health, 10(2), pp. 83-97, Mar.-Apr. 2007.
Cooney et al.; Electrowetting droplet microfluidics on a single planar surface, Microfluid. Nanofluid., 2(5), pp. 435-446; Sep. 2006.

(56) References Cited

OTHER PUBLICATIONS

Coregenomics; How do SPRI beads work; 31 pages; retrieved from the internet (http://core-genomics.blogspot.com/2012/04/how-do-spri-beads-work.html); Apr. 28, 2012.
Cottam et al.; Accelerated synthesis of titanium oxide nanostructures using microfluidic chips; Lab on a Chip; 7(2); pp. 167-169; Feb. 2007.
Crabtree et al.; Microchip injection and separation anomalies due to pressure effects, Anal. Chem., 73(17), pp. 4079-4086, Sep. 2001.
Cunningham; Testosterone replacement therapy for late-onset hypogonadism. Nature Clinical Practice Urology, 3(5), pp. 260-267, May 2006.
Cuzick; Chemoprevention of breast cancer. Women's Health, 2(6), pp. 853-861, Nov. 2006.
Dahlin et al.; Poly(dimethylsiloxane)-based microchip for two-dimensional solid-phase extraction-capillary electrophoresis with an integrated electrospray emitter tip, Anal. Chem., 77(16), pp. 5356-5363, Aug. 2005.
Dambrot; Of microchemistry and molecules: Electronic microfluidic device synthesizes biocompatible probes; 4 pages, retrieved from the internet (https://phys.org/news/2012-01-microchemistry-molecules-electronic-microfluidic-device.html); Jan. 26, 2012.
Danton et al.; Porphyrin profiles in blood, urine and faeces by HPLC/electrospray ionization tandem mass spectrometry. Biomedical Chromatography, 20(6-7), pp. 612-621, Jun.-Jul. 2006.
Davoust et al.; Evaporation rate of drop arrays within a digital microfluidic system; Sensors and Actuators B Chemical; 189; pp. 157-164; Dec. 2013.
Davoust et al.; Evaporation Rate of Drop Arrays within a Digital Microsystem; Procedia Engineering; vol. 47; pp. 1-4; Jan. 1, 2012.
De Mesmaeker et al.; Comparison of rigid and flexible backbones in antisense oligonucleotides; Bioorganic & Medicinal Chem. Lett; 4(3); pp. 395-398; Feb. 1994.
Deligeorgiev et al.; Intercalating Cyanine Dyes for Nucleic Acid Detection; Recent Pat Mat Sci; 2(1); pp. 1-26; Jan. 2006.
Dempcy et al., Synthesis of a thymidyl pentamer of deoxyribonucleic guanidine and binding studies with DNA homopolynucleotides, Proc. Natl. Acad. Sci., 92(13), pp. 6097-6101, Jun. 1995.
Deng et al.; Rapid determination of amino acids in neonatal blood samples based on derivatization with isobutyl chloroformate followed by solid-phase microextraction and gas chromatography/mass spectrometry. Rapid Communications in Mass Spectrometry, 18(1), pp. 2558-2564, Nov. 2004.
Denneulin et al.; Infra-red assisted sintering of inkjet printed silver tracks on paper substrates; J Nanopart Res; 13(9); pp. 3815-3823; Sep. 2011.
Dibbelt et al.; Determination of natural and synthetic estrogens by radioimmunoassay: Comparison of direct and extraction methods for quantification of estrone in human serum. Clinical Laboratory, 44(3), 137-143, Mar. 1998.
Dietzen et al.; National academy of clinical biochemistry laboratory medicine practice guidelines: follow-up testing for metabolic disease identified by expanded newborn screening using tandem mass spectrometry; executive summary, Clinical Chemistry, 55(9), pp. 1615-1626, Sep. 2009.
Diver et al.; Warning on plasma oestradiol measurement. Lancet, 330(8567), p. 1097, Nov. 1987.
Divino Filho et al.; Simultaneous measurements of free amino acid patterns of plasma, muscle and erythrocytes in healthy human subjects, Clinical Nutrition, 16(6), pp. 299-305, Dec. 1997.
Djerassi; Chemical birth of the pill. American Journal of Obstetrics and Gynecology, 194(1), pp. 290-298, Jan. 2006.
Dobrowolski et al.; DNA microarray technology for neonatal screening, Acta Paediatrica Suppl, 88(432), pp. 61-64, Dec. 1999.
Doebler et al.; Continuous-flow, rapid lysis devices for biodefense nucleic acid diagnostic systems; Journal of the Association for Laboratory Automation; 14(3); pp. 119-125; Jun. 2009.
Dong et al.; Highly sensitive multiple microRNA detection based on flourescence quenching of graphene oxide and isothermal strand-displacement polymerase reaction; Anal Chem; 84; pp. 4587-4593; Apr. 2012.
Dryden et al.; Integrated digital microfluidic platform for voltammetric analysis; Analytical Chemistry; 85(18); pp. 8809-8816; Sep. 2013.
Duffy et al.; Rapid prototyping of microfluidic systems in Poly (dimethylsiloxane), Anal. Chem., 70(23), pp. 4974-4984, Dec. 1998.
Edgar et al.; Capillary electrophoresis separation in the presence of an immiscible boundary for droplet analysis, Anal. Chem., 78(19), pp. 6948-6954 (author manuscript, 15 pgs.), Oct. 2006.
Egholm et al., PNA hybridizes to complementary oligonucleotides obeying the Watson-Crick hydrogen-bonding rules, Nature, 365(6446), pp. 566-568, Oct. 1993.
Egholm et al., Recognition of guanine and adenine in DNA by cytosine and thymine containing peptide nucleic acids (PNA), J. Am. Chem. Soc., 114(24), pp. 9677-9678; Nov. 1992.
Ehrmann; Polycystic ovary syndrome. New England Journal of Medicine; 352(12); pp. 1223-1236; Mar. 2005.
Ekstrom et al., Miniaturized solid-phase extraction and sample preparation for MALDI MS using a microfabricated integrated selective enrichment target, Journal of Proteome Research, 5(5), pp. 1071-1081, May 2006.
Ekstrom et al., Polymeric integrated selective enrichment target (ISET) for solid-phase-based sample preparation in MALDI-TOF MS, Journal of Mass Spectrometry, 42(11), pp. 1445-1452, Nov. 2007.
Ekstrom et al., On-chip microextraction for proteomic sample preparation of in-gel digests, Proteomics, 2(4), pp. 413-421, Apr. 2002.
El-Ali et al.; Cells on chips; Nature (2006) insight Review; 442(7101); pp. 403-411; Jul. 2006.
Fair; Digital microfluidics: Is a true lab-on-a-chip possible?; Microfuid. Nanofluid.; 3(3); pp. 245-281; Jun. 2007.
Falk et al.; Measurement of Sex Steroid Hormones in Breast Adipocytes: Methods and Implications; Cancer Epidemiol Biomarkers Prev; 17(8); pp. 1891-1895; Aug. 2008.
Fan et al.; Cross-scale electric manipulations of cells and droplets by frequency-modulated dielectrophoresis and electrowetting; Lab Chip; 8(8); pp. 1325-1331; Aug. 2008.
Fan et al.; Electrically Programmable Surfaces for Configurable Patterning of Cells; Advanced Materials; 20(8); pp. 1418-1423; Apr. 2008.
Fan et al.; Integrated barcode chips for rapid, multiplexed analysis of proteins in microliter quanties of blood; Nature Biotechnology; 26(12); pp. 1373-1378; 15 pages (Author Manuscript); Dec. 2008.
Faure et al.; Improved electrochemical detection of a transthyretin synthetic peptide in the nanomolar range with a two-electrode system integrated in a glass/PDMS microchip; Lab on a Chip; 14(15); pp. 2800-2805, Aug. 2014.
Fobel et al.; DropBot: An open-source digital microfluidic control system with precise control of electrostatic driving force and instantaneous drop velocity measurement; Applied Physics Letters; 102(19); 193513 (5 pgs.); May 2013.
Foote et al., Preconcentration of proteins on microfluidic devices using porous silica membranes, Analytical Chemistry, 77(1), pp. 57-63, Jan. 2005.
Freire et al.; A practical interface for microfluidics and nanoelectrospray mass spectrometry, Electrophoresis, 29(9), pp. 1836-1843, May 2008.
Fridley et al., Controlled release of dry reagents in porous media for tunable temporal and spatial distribution upon rehydration, Lab Chip, 12(21), pp. 4321-4327 (author manuscript, 14 pgs.), Nov. 2012.
Fu et al., Controlled Reagent Transport in Disposable 2D Paper Networks, Lab. Chip, 10(7), pp. 918-920 (author manuscript, 9 pgs.), Apr. 2010.
Gao et al.; Unusual conformation of a 3'-thioformacetal linkage in a DNA duplex; J. Biomol. NMR; 4(1); pp. 17-34; Jan. 1994.
Gentili et al.; Analysis of free estrogens and their conjugates in sewage and river waters by solid-phase extraction then liquid

(56) References Cited

OTHER PUBLICATIONS chromatography-electrospray-tandem mass spectrometry. Chromatographia 56(1), pp. 25-32, Jul. 2002.

Gerasimova et al.; Fluorometric method for phenylalanine microplate assay adapted for phenylketonuria screening, Clinical Chemistry, 35(10), pp. 2112-2115, Oct. 1989.

Gong et al., All-Electronic Droplet Generation On-Chip With Real-Time Feedback Control for EWOD Digital Microfluidics, Lab Chip, 8(6), pp. 898-906 (author manuscript, 20 pgs.), Jun. 2008.

Gong et al.; Portable digital microfluidics platform with active but disposable lab-on-chip; 17th IEEE International Conference on Micro Electro Mechanical Systems; Maastricht, Netherlands; pp. 355-358; Jan. 24-29, 2004.

Gong et al.; Two-dimensional digital microfluidic system by multilayer printed circuit board, 18th IEEE International Conference on Micro Electro Mechanical Systems (MEMS 2005); IEEE; pp. 726-729; Jan. 30-Feb. 3, 2005.

Goto et al.; Colorimetric detection of loop-mediated isothermal amplification reaction by using hydroxy naphthol blue; Biotechniques; 46(3); pp. 167-172; Mar. 2009.

Gottschlich et al.; Integrated microchip-device for the digestion, separation and postcolumn labeling of proteins and peptides, J. Chromatogr. B, 745(1), pp. 243-249, Aug. 2000.

Govindarajan et al., A low cost point-of-care viscous sample preparation device for molecular diagnosis in the developing world; an example of microfluidic origami, Lab Chip, 12(1), pp. 174-181, Jan. 2012.

Green et al.; Neonatal screening by DNA microarray: spots and chips, Nature Reviews Genetics, 6(2), pp. 147-151, Feb. 2005.

Hatch et al., Integrated preconcentration SDS-Page of proteins in microchips using photopatterned cross-linked polyacrylamide gels, Analytical Chemistry, 78(14), pp. 4976-4984, Jul. 2006.

He et al. (ed); Food microbiological inspection technology; Chapter 5: Modern food microbiological inspection technology; China Quality Inspection press; pp. 111-113; (English Translation included) Nov. 2013.

Henderson et al.; Estrogens as a cause of human cancer: The Richard and Hinda Rosenthal Foundation award lecture. Cancer Res, 48(2), pp. 246-253, Jan. 1988.

Hennequin et al.; Synthesizing microcapsules with controlled geometrical and mechanical properties with microfluidic double emulsion technology; Langmuir; 25(14); pp. 7857-7861; Jul. 2009.

Herdewijn et al.; 2'-5'-Oligoadenylates (2-5A) as Mediators of Interferon Action. Synthesis and Biological Activity of New 2-5A Analogues. E. De Clerq (ed.) Frontiers in Microbiology, 231-232, Springer, Dordrecht Jan. 1987.

Hertz et al.; Estrogen-progestogen combinations for contraception. Journal of the American Medical Association, 198(9), pp. 1000-1006, Nov. 1966.

Hong et al.; Three-dimensional digital microfluidic manipulation of droplets in oil medium; Scientific Reports; 5 (Article No. 10685); 5 pgs.; Jun. 2015.

Horn et al.; Oligonucleotides with alternating anionic and cationic phosphoramidate linkages: Synthesis and hybridization of stereouniform isomers; Tetrahedron Lett.; 37(6); pp. 743-746; Feb. 1996.

Hou et al.; Microfluidic devices for blood fractionation; Micromachines; 2(3); pp. 319-343; Jul. 20, 2011.

Huh et al.; Reversible Switching of High-Speed Air-Liquid Two-Phase Flows Using Electrowetting-Assisted Flow-Pattern Change, J. Am. Chem. Soc., 125, pp. 14678-14679; Dec. 2003.

Ihalainen et al.; Application of paper-supported printed gold electrodes for impedimetric immunosensor development; Biosensors; 3(1); pp. 1-17; Mar. 2013.

Jacobson et al.; High-Speed Separations on a Microchip, Anal. Chem., 66(7), pp. 1114-1118, Apr. 1994.

Jacobson et al.; Precolumn Reactions with Electrophoretic Analysis Integrated on a Microchip, Anal. Chem., 66(23), pp. 4127-4132, Dec. 1994.

Jebrail et al., Combinatorial Synthesis of Peptidomimetics Using Digital Microfluidics, J. Flow Chem., 2(3), pp. 103-107; (online) Aug. 2012.

Jebrail et al., Let's get digital: digitizing chemical biology with microfluidics, Curr. Opin. Chem. Biol., 14(5), 574-581, Oct. 2010.

Jebrail et al., Synchronized synthesis of peptide-based macrocycles by digital microfluidics, Angew. Chem. Int. Ed. Eng., 49(46), pp. 8625-8629, Nov. 2010.

Jebrail et al., World-to-digital-microfluidic interface enabling extraction and purification of RNA from human whole blood, Analytical Chemistry, 86(8), pp. 3856-3862, Apr. 2014.

Jebrail et al.; A Solvent Replenishment Solution for Managing Evaporation of Biochemical Reactions in Air-Matrix Digital Microfluidics Devices, Lab on a Chip, 15(1), pp. 151-158; Jan. 2015.

Jebrail et al.; Digital Microfluidic Method for Protein Extraction by Precipitation; Analytical Chemistry; 81(1); pp. 330-335; Jan. 2009.

Jebrail et al.; Digital Microfluidics for Automated Proteomic Processing, Journal of Visualized Experiments, 33 (e1603), 5 pgs., Nov. 2009.

Jebrail et al.; Digital microfluidics: a versatile tool for applications in chemistry, biology and medicine; Lab Chip; 12 (14); pp. 2452-2463; Jul. 2012.

Jemere et al., An integrated solid-phase extraction system for sub-picomolar detection, Electrophoresis, 23(20), pp. 3537-3544, Oct. 2002.

Jenkins et al., The biosynthesis of carbocyclic nucleosides; Chem. Soc. Rev.; 24(3); pp. 169-176; Jan. 1995.

Jessome et al.; Ion Suppression: A Major Concern in Mass Spectrometry. LC-GC North America, 24(5), pp. 498-510, May 2006.

Jia et al.; Ultrasensitive detection of microRNAs by exponential isothermal amplification; Angew. Chem. Int. Ed. Engl.; 49(32); pp. 5498-5501; Jul. 2010.

Jung et al.; Hybridization of Alternating Cationic/Anionic Oligonucleotides to RNA Segments; Nucleosides & Nucleotides; 13(6-7); pp. 1597-1605; Jul. 1994.

Kaaks et al.; Postmenopausal serum androgens, oestrogens and breast cancer risk: The European prospective investigation into cancer and nutrition. Endocrine-Related Cancer, 12(4), pp. 1071-1082, Dec. 2005.

Keng et al., Micro-chemical synthesis of molecular probes on an electronic microfluidic device,PNAS, 109(3), pp. 690-695; Jan. 2012.

Kiedrowski et al., Parabolic Growth of a Self-Replicating Hexadeoxynucleotide Bearing a 3'-5'-Phosphoamidate Linkage; Angew. Chemie Intl. Ed.; 30(4); pp. 423-426; Apr. 1991.

Kim et al.; Automated digital microfluidic sample preparation for next-generation DNA sequencing; JALA; Journal of the Association for Laboratory Automation; 16(6); pp. 405-414; Dec. 2011.

Kim et al., A Microfluidic DNA Library Preparation Platform for Next-Generation Sequencing, PLoS ONE, 8(7), Article ID: e68988; 9 pgs., Jul. 2013.

Kim et al.; Microfabricated Monolithic Multinozzle Emitters for Nanoelectrospray Mass Spectrometry; Anal Chem; 79(10); pp. 3703-3707; May 2007.

Koster et al.; Drop-based microfluidic devices for encapsulation of single cells; Lab on a Chip; 8(7); pp. 1110-1115; Jul. 2008.

Kralj et al.; Integrated continuous microfluidic liquid-liquid extraction. Lab on a Chip, 7(2), pp. 256-263, Feb. 2007.

Kutter et al., Solid phase extraction on microfluidic devices, Journal of Microcolumn Separations, 12(2), pp. 93-97, Jan. 2000.

Kutter et al., Solvent-Programmed Microchip Open-Channel Electrochromatography, Analytical Chemistry, 70(15), pp. 3291-3297, Aug. 1998.

Labrie et al.; Androgen glucuronides, instead of testosterone, as the new markers of androgenic activity in women. The Journal of Steroid Biochemistry and Molecular Biology, 99(4-5), pp. 182-188, Jun. 2006.

Labrie; Intracrinology. Molecular and Cellular Endocrinology, 78(3), pp. C113-C118, Jul. 1991.

Lamar et al.; Serum sex hormones and breast cancer risk factors in postmenopausal women. Cancer Epidemiol Biomarkers Prev, 12(4), pp. 380-383, Apr. 2003.

(56) References Cited

OTHER PUBLICATIONS

Langevin et al., A rapid and unbiased method to produce strand-specific RNA-Seq libraries from small quantities of starting materiaRNA Biol., 10(4), pp. 502-515, (online) Apr. 2013.

Lawyer et al.; High-level expression, purification, and enzymatic characterization of full-length Thermus aquaticus DNA polymerase and a truncated form deficient in 5' to 3' exonuclease activity; Genome Res; 2(4); pp. 275-287; May 1993.

Lawyer et al.; Isolation, characterization, and expression in *Escherichia coli* of the DNA polymerase gene from Thermus aquaticus; J. Biol. Chem.; 264; pp. 6427-6437; Apr. 1989.

Lebrasseur et al.; Two-dimensional electrostatic actuation of droplets using a single electrode panel and development of disposable plastic film card; Sensors and Actuators A; 136(1); pp. 368-386; May 2007.

Lee et al.; Electrowetting and electrowetting-on-dielectric for microscale liquid handling, Sens. Actuators A, 95(2), pp. 259-268, Jan. 2002.

Lee et al.; Removal of bovine serum albumin using solid-phase extraction with in-situ polymerized stationary phase in a microfluidic device; Journal of Chromatography A; 1187(1-2); pp. 11-17; Apr. 2008.

Lee et al.; Surface-Tension-Driven Microactuation Based on Continuous Electrowetting; J. Microelectromechanical Systems; 9(2); pp. 171-180; Jun. 2000.

Leriche et al.; Cleavable linkers in chemical biology; Bioorganic & Medicinal Chemistry; 20(2); pp. 571-582; Jan. 15, 2012.

Letsinger et al., Cationic oligonucleotides, J. Am. Chem. Soc., 110(13), pp. 4470-4471, Jun. 1988.

Letsinger et al., Effects of pendant groups at phosphorus on binding properties of d-ApA analogues, Nucl. Acids Res., 14(8), pp. 3487-3499, Apr. 1986.

Letsinger et al., Phosphoramidate analogs of oligonucleotides, J. Org. Chem., 35(11), pp. 3800-3803, Nov. 1970.

Lettieri et al., A novel microfluidic concept for bioanalysis using freely moving beads trapped in recirculating flows, Lab on a Chip, 3(1), pp. 34-39, Feb. 2003.

Levy et al.; Genetic screening of newborns, Annual Review of Genomics and Human Genetics, 1, pp. 139-177, Sep. 2000.

Li et al., A perspective on paper-based microfluidics: Current status and future trends, Biomicrofluidics, 6(1), pp. 011301 (13 pgs), Mar. 2012.

Li et al., Application of microfluidic devices to proteomics research: identification of trace-level protein digests and affinity capture of target peptides, Molecular & cellular Proteomics, 16(2), pp. 157-168, Feb. 2002.

Li et al., Paper-based microfluidic devices by plasma treatment, Anal. Chem., 80(23), pp. 9131-9134, Nov. 2008.

Li et al.; A Low-Cost and High resolution droplet position detector for an intelligent electrowetting on dielectric device; Journal of Lab. Automation 2015; 20(6); pp. 663-669; Dec. 2015.

Li et al.; One-step ultrasensitive detection of microRNAs with loop-mediated isothermal amplification (LAMP); Chem Commun; 47(9); pp. 2595-2597; Mar. 2011.

Li et al.; Test structure for characterizing low voltage coplanar EWOD system; IEEE Transaction on Semiconductor Manufacturing: IEEE Service Center; Piscataway, NJ.; 22(1); pp. 88-95; Feb. 4, 2009.

Liana et al.; Recent Advances in Paper-Based Sensors; Sensors; 12(9); pp. 11505-11526; Aug. 2012.

Link et al.; Electric Control of Droplets in Microfluidic Devices; Angew Chem Int Ed Engl; 45(16); pp. 2556-2560; Apr. 2006.

Liu et al., Three-dimensional paper microfluidic devices assembled using the principles of origami, JACS, 133(44), pp. 17564-17566, Nov. 2011.

Liu et al.; Attomolar ultrasensitive microRNA detection by DNA-scaffolded silver-nanocluster probe based on isothermal amplification; Anal Chem; 84(12); pp. 5165-5169; Jun. 2012.

Lizardi et al.; Mutation detection and single-molecule counting using isothermal rolling-circle amplification; Nat. Genet.; 19(3); pp. 225-232; Jul. 1998.

Locascio et al.; Surface chemistry in polymer microfluidic systems; in Lab-on-a-Chip; Elsevier Science; 1st Ed.; pp. 65-82; Oct. 2003.

Loeber; Neonatal screening in Europe; the situation in 2004, Journal of inherited Metabolic Disease, 30(4), pp. 430-438, Aug. 2007.

Lohman et al.; Efficient DNA ligation in DNA-RNA hybrid helices by Chlorella virus DNA ligase; Nucleic Acids Research; 42(3); pp. 1831-1844; Nov. 2013.

Luk et al.; Pluronic Additives: A Solution to Sticky Problems in Digital Microfluidics, Langmuir, 24(12), pp. 6382-6389, Jun. 2008.

Luk et al.; A digital microfluidic approach to proteomic sample processing; Analytical Chemistry; 81(11); pp. 4524-4530; Jun. 2009.

Mag et al., Synthesis and selective cleavage of an oligodeoxynucleotide containing a bridged internucleotide 5'-phosphorothioate linkage, Nucleic Acids Res., 19(7), pp. 1437-1441, Apr. 1991.

Mais et al.; A solvent replenishment solution for managing evaporation of biochemical reactions in air-matrix digital microfluidics devices; Lab on a Chip; 15(1); pp. 151-158; Jan. 2015.

Makamba et al.; Surface modification of poly(dimethylsiloxane) microchannels; Electrophoresis; 24(21); pp. 3607-3619, Nov. 2003.

Malloggi et al.; Electrowetting—A versatile tool for controlling microdrop generation, Eur. Phys. J. E, 26(1), pp. 91-96, May 2008.

Mandl et al.; Newborn screening program practices in the United States: notification, research, and consent, Pediatrics, 109(2), pp. 269-273, Feb. 2002.

Maroney et al.; A Rapid, quantitative assay for direct detection of microRNAs and other small RNAs using splinted ligation; RNA; 13(6); pp. 930R936; Jun. 2007.

Maroney et al.; Direct detection of small RNAs using splinted ligation; Nat. Protocols3(2); pp. 279-287; Jan. 2008.

Marre et al.; Synthesis of micro and nanostructures in microfluidic systems; Chemical Society Reviews; 39(3); pp. 1183-1202; Mar. 2010.

Martinez et al., Simple Telemedicine for Developing Regions: Camera Phones and Paper-Based Microfluidic Devices for Real-Time, Off-Site Diagnosis, Anal. Chem., 80(10), pp. 3699-3707, May 2008.

Martinez et al., Three-dimensional microfluidic devices fabricated in layered paper and tape, PNAS, 105(50), pp. 19606-19611, Dec. 2008.

Martinez et al.; Patterned paper as a platform for inexpensive low-volume, portable bioassays, Angewandte Chemie, 46(8), pp. 1318-1320, Feb. 2007.

Martinez-Sanchez et al.; MicroRNA Target Identification—Experimental Approaches; Biology; 2; pp. 189-205; Jan. 2013.

Matern et al.; Reduction of the false-positive rate in newborn screening by implementation of MS/MS-based second-tier tests: the Mayo Clinic experience (2004-2007), Journal of Inherited Metabolic Disease, 30(4), pp. 585-592, Aug. 2007.

Mauney, Thermal Considerations for Surface Mount Layouts, in Texas Instruments Portable Power Supply Design Seminar, 16 pgs., 2006.

Mega; Heterogenous ion-exchange membranes Ralex; 3 pgs.; retrieved Mar. 1, 2016 from the internet: http://www.mega.cz/heterogenous-ion-exchange-membranes-ralex.html.

Meier et al., The photochemistry of stilbenoid compounds and their role in materials technology, Chem. Int. Ed. Engl., 31(11), pp. 1399-1420, Nov. 1992.

Mellors et al.; Fully Integrated Glass Microfluidic Device for Performing High-Efficiency Capillary Electrophoresis and Electrospray Ionization Mass Spectrometry, Analytical Chemistry, 80(18), pp. 6881-6887 (Author Manuscript, 18 pgs.), Sep. 2008.

Michigan Dept. of Community Health; Specimen collection procedure from Michigan Newborn Screening Program, 37 pgs., (retrieved Feb. 9, 2017 online: http://web.archive.org/web/20100715000000*/http://www.michigan.gov/documents/Bloodco2_60773_7.pdf) Jul. 2009.

Miller et al.; A digital microfluidic approach to homogeneous enzyme assays, Anal. Chem., 80(5), pp. 1614-1619, Mar. 2008.

Millington et al.; Digital Microfluidics: A Future Technology in the Newborn Screening Laboratory?, Seminars in Perinatology, 34(2), pp. 163-169 (Author Manuscript, 14 pgs.), Apr. 2010.

(56) References Cited

OTHER PUBLICATIONS

Millington et al.; Digital Microfluidics: A novel platform for multiplexed detection of LSDs with potential for newborn screening (conference presentation); Oak Ridge Conference; 15 pgs.; 2009.

Millington et al.; Tandem mass spectrometry: a new method for acylcarnitine profiling with potential for neonatal screening for inborn errors of metabolism, Journal of Inherited Metabolic Disease, 13(3), pp. 321ý324, May 1990.

Millington et al.; The Analysis of Diagnostic Markers of Genetic Disorders in Human Blood and Urine Using Tandem Mass Spectrometry With Liquid Secondary Ion Mass Spectrometry, International Journal of Mass Spectrometry, 111, pp. 211-228, Dec. 1991.

Miralles et al.; A Review of Heating and Temperature Control in Microfluidic Systems: Techniques and Applications; Diagnostics; 3; pp. 33-67; Jan. 2013.

Mitchell et al.; Circulating microRNAs as stable blood-based markers for cancer detection; Proc Nat Acad Sci; 105(30); pp. 10513-10518; Jul. 2008.

Moon et al.; An integrated digital microfluidic chip for multiplexed proteomic sample preparation and analysis by MALDI-MS. Lab Chip, 6(9), pp. 1213-1219, Sep. 2006.

Moqadam et al.; The Hunting of Targets: Challenge in miRNA Research; Leukemia; 27(1); pp. 16-23; Jan. 2013.

Mousa et al.; Droplet-scale estrogen assays in breast tissue, blood, and serum, Science Translational Medicine, 1(1), 6 pgs., Oct. 2009.

Murran et al.; Capacitance-based droplet position estimator for digital microfluidic devices; Lab Chip; 12(11); pp. 2053-2059; May 2012.

Nakamura et al.; Simple and accurate determination of CYP2D6 gene copy number by a loop-mediated isothermal amplification method and an electrochemical DNA chip; Clinica Chimica Acta; 411(7-8); pp. 568-573; Apr. 2010.

Nelson et al., Incubated protein reduction and digestion on an EWOD digital microfluidic chip for MALDI-MS, Analytical Chemistry, 82(23), pp. 9932-9937, Dec. 2010.

Newborn Screening Ontario, The newborn screening ontario unsatisfactory sample indicator (educational resource), 3 pgs., retrieved online: https:/www.newbornscreening.on.ca/en/health-care-providers/submitters/report-cards/nso_unsatisfatory_sample_indicator_jan_2017, (web address was available to applicant(s) at least as of Jan. 2010).

Ng et al., Digital microfluidic magnetic separation for particle-based immunoassays, Anal. Chem., 84(20), 8805-8812, Oct. 2012.

Nge et al.; Advances in microfluidic materials, functions, integration, and applications. Chemical reviews; 113(4); pp. 2550-2583; Apr. 10, 2013.

Nilsson et al.; RNA-templated DNA ligation for transcript analysis; Nucl. Acid Res.; 29(2); pp. 578-581; Jan. 2001.

Njiru; Loop-Mediated Isothermal Amplification Technology: Towards Point of Care Diagnostics; PLoS; 6(6); pp. e1572 (4 pgs.); Jun. 2012.

Notomi et al.; Loop-mediated isothermal amplification of DNA; Nucleic Acid Research; 28(12); p. e63 (7 pgs.); Jun. 2000.

Okubo et al.; Liquid-liquid extraction for efficient synthesis and separation by utilizing micro spaces. Chemical Engineering Science, 63(16), pp. 4070-4077, Aug. 2008.

Oleschuk et al., Trapping of bead-based reagents within microfluidic systems: On-chip solid-phase extraction and electrochromatography, Analytical Chemistry, 72(3), pp. 585-590, Feb. 2000.

Padilla et al.; Newborn screening in the Asia Pacific region, Journal of Inherited Metabolic Disease, 30(4), pp. 490-506, Aug. 2007.

Paik et al., Coplanar digital microfluidics using standard printed circuit board processes, in Proceedings 9th Int'l Conf Miniaturized Systems for Chemistry and Life Sciences (MicroTAS 2005), Boston, MA, USA, pp. 566-568, Oct. 9-13, 2005.

Paneri et al.; Effect of change in ratio of electrode to total pitch length in EWOD based microfluidic system; InComputer Applications and Industrial Electronics (ICCAIE); 2010 International Conference; pp. 25-28; Dec. 5, 2010.

Parida et al.; Rapid detection and differentiation of Dengue virus serotypes by a real-time reverse transcription-loop-mediated isothermal amplification assay; J Clinical Microbiology; 43(6); pp. 2895-2903; Jun. 2005.

Pauwels et al., Biological-Activity of New 2-5a Analogs, Chemica Scripta, 26(1), pp. 141-145, Mar. 1986.

Peltonen et al.; Printed electrodes on tailored paper enable electrochemical functionalization of paper; TAPPI Nanotechnology Conference; Espoo, Finland; 20 pgs.; Sep. 2010.

Peterschmitt et al.; Reduction of false negative results in screening of newborns for homocystinuria, New England Journal of Medicine, 341(21), 1572-1576, Nov. 1999.

Petersen et al., On-chip electro membrane extraction, Microfluidics and Nanofluidics, 9(4), pp. 881-888, Oct. 2010.

Pitt et al.; Hormone replacement therapy for osteoporosis. Lancet, 335 (8695), p. 978, Apr. 1990.

Pollack et al.; Electrowetting-based actuation of droplets for integrated microfluidics; Lab on a Chip; 2(2); pp. 96-101; May 2002.

Pollack et al.; Electrowetting-based actuation of liquid droplets for microfluidic applications, Appl. Phys. Lett., 77(11), pp. 1725-1726, Sep. 2000.

Provincial Health Services Authority (British Columbia Perinatal Health Program), Perinatal Services BC Neonatal Guideline 9: Newborn Screening, 29 pgs., (retrieved Feb. 9, 2017 online: http://www.perinatalservicesbc.ca/health-professionals/guidelines-standards/newborn) guideline revised: Dec. 2010.

Ratcharak et al.; Surface coating with poly (trifluoroethyl methacrylate) through rapid expansion of supercritical CO2 solutions; The Journal of Supercritical Fluids; vol. 89; pp. 106-112; May 1, 2014.

Rahhal et al.; The impact of assay sensitivity in the assessment of diseases and disorders in children. Steroids, 73(13), pp. 1322-1327, Dec. 2008.

Rashad; Clinical applications of tandem mass spectrometry: ten years of diagnosis and screening for inherited metabolic diseases, Journal of Chromatography B: Biomedical Sciences and Applications, 758(1), pp. 27-48, Jul. 2001.

Rashed et al.; Diagnosis of inborn errors of metabolism from blood spots by acylcarnitines and amino acids profiling using automated electrospray tandem mass spectrometry, Pediatric Research, 38(3), 324-331, Sep. 1995.

Rawls, Optimistic About Antisense: Promising clinical results and chemical strategies for further improvements delight antisense drug researchers; Chemical & Engineering News; 75(22); pp. 35-39; Jun. 2, 1997.

Ren et al., Automated on-chip droplet dispensing with volume control by electro-wetting actuation and capacitance metering, Sens. Actuator B Chem., 98(2-3), pp. 319-327, Mar. 2004.

Ren et al.; Design and testing of an interpolating mixing architecture for electrowetting-based droplet-on-chip chemical dilution; 12th International Conference on Transducers, Solid-State Sensors, Actuators and Microsystems; vol. 2; Boston, MA, USA; pp. 619-622; Jun. 8-12, 2003.

Ro et al.; Poly (dimethylsiloxane) microchip for precolumn reaction and micellar electrokinetic chromatography of biogenic amines, Electrophoresis, 23(7-8), pp. 1129-1137, Apr. 2002.

Roman et al.; Fully integrated microfluidic separations systems for biochemical analysis, J. Chromatogr. A, 1168(1-2), pp. 170-188, Oct. 2007.

Roman et al.; Sampling and Electrophoretic Analysis of Segmented Flow Streams in a Microfluidic Device, Anal. Chem., 80(21), pp. 8231-8238 (author manuscript, 19 pgs.), Nov. 2008.

Sabourin et al.; Interconnection blocks: a method for providing reusable, rapid, multiple, aligned and planar microfluidic interconnections; Journal of Micromechanics and Microengineering; 19(3); 10 pages; doi: 10.1088/0960-1317/19/3/035021; Feb. 18, 2009.

Sadeghi et al.; On Chip Droplet Characterization: A Practical, High-Sensitivity Measurement of Droplet Impedance in Digital Microfluidics; Anal. Chem.; 84(4); pp. 1915-1923; Feb. 2012.

Sahai et al.; Newborn screening, Critical Reviews in Clinical Laboratory Sciences, 46(2), pp. 55-82, (online) Mar. 2009.

Samsi et al.; A Digital Microfluidic Electrochemical Immunoassay; Lab on a Chip; 14(3); pp. 547-554; Feb. 2014.

(56) References Cited

OTHER PUBLICATIONS

Sanghvi & Cook (Ed.); Carbohydrate Modifications in Antisense Research; Chapters 2 and 3, American Chemical Society, Washington DC; (207th National Meeting of the American Chemical Society Mar. 13-17, 1994, San Jose, CA); Dec. 1994.

Sanghvi & Cook (Ed.); Carbohydrate Modifications in Antisense Research; Chapters 6 and 7, American Chemical Society, Washington DC; (207th National Meeting of the American Chemical Society Mar. 13-17, 1994, San Jose, CA); Dec. 1994.

Santen et al.; Superiority of gas chromatography/tandem mass spectrometry assay (GC/MS/MS) for estradiol for monitoring of aromatase inhibitor therapy. Steroids. 72(8), pp. 666-671, Jul. 2007.

Sasano et al.; From Endocrinology to Intracrinology. Endocr Pathol, 9(1), pp. 9-20, Spring 1998.

Satoh et al.; Electrowetting-based valve for the control of the capillary flow, J. Appl. Phys., 103(3), 034903, Feb. 2008.

Satoh et al.; On-chip microfluidic transport and mixing using electrowetting and incorporation of sensing functions, Anal. Chem., 77(21), pp. 6857-6863, Nov. 2005.

Sawai et al., Synthesis and properties of oligoadenylic acids containing 2 ?- 5? phosphoramide linkage, Chem. Lett., 13(5), pp. 805-808, May 1984.

Schertzer et al.; Using capacitance measurements in EWOD devices to identify fluid composition and control droplet mixing; Sens. Actuators B; 145(1); pp. 340-347; Mar. 2010.

Scriver_Commentary; A Simple Phenylalanine Method for Detecting Phenylketonuria in Large Populations of Newborn Infants by Guthrie et al., Pediatrics, 32(3), 338-343, Sep. 1963.

Shah et al., On-demand droplet loading for automated organic chemistry on digital microfluidics, Lab Chip, 13(14), pp. 2785-2795, Jul. 2013.

Shamsi et al.; A digital microfluidic electrochemical immunoassay; Lab on a Chip; 14(3); pp. 547-554; (the year of publication is sufficiently earlier than the effective U.S. filing date and any foreign priority date so that the particular month of publication is not in issue) 2014.

Shih et al., A feedback control system for high-fidelity digital microfluidics, Lab Chip, 11(3), pp. 535-540, Feb. 2011.

Simpson et al.; Estrogen—the Good, the Bad, and the Unexpected. Endocr Rev, 26(3), pp. 322-330; May 2005.

Sinha et al., A Versatile Automated Platform for Micro-scale Cell Stimulation Experiments, J. Vis. Exp., e50597, 8 pgs., Aug. 2013.

Sinton et al.; Electroosmotic velocity profiles in microchannels, Colloids Surf. A, 222(1-3), pp. 273-283, Jul. 2003.

Skendzel, Rubella immunity: Defining the level of protective antibody, Am. J. Clin. Pathol., 106(2), 170-174, Aug. 1996.

Smith et al.; Diagnosis and Management of Female Infertility. Journal of the American Medical Association 290(13), pp. 1767-1770, Oct. 2003.

Sooknanan et al., Nucleic Acid Sequence-Based Amplification, Ch. 12; Molecular Methods for Virus Detection (1st Ed.), Academic Press, Inc., pp. 261-285; Jan. 1995.

Sprinzl et al., Enzymatic incorporation of ATP and CTP analogues into the 3' end of tRNA, Eur. J. Biochem., 81(3), pp. 579-589, Dec. 1977.

Srinivasan et al.; An integrated digital microfluidic lab-on-a-chip for clinical diagnostics on human physiological fluids, Lab Chip, 4(4), pp. 310-315, Aug. 2004.

Stanczyk et al.; Standardization of Steroid Hormone Assays Why, How, and When?, Cancer Epidemiol Biomarkers Prev, 16(9), pp. 1713-1719, Sep. 2007.

Steckl et al.; Flexible Electrowetting and Electrowetting on Flexible Substrates; Proc. SPIE 7956; Advances in Display Technologies; and E-papers and Flexible Displays; 795607 (6 pgs.); Feb. 2011.

Stegink et al.; Plasma amino acid concentrations and amino acid ratios in normal adults and adults heterozygous for phenylketonuria ingesting a hamburger and milk shake meal, American Journal of Clinical Nutrition, 53(3), pp. 670-675, Mar. 1991.

Sun et al.; Rapid and direct microRNA quantification by an enzymatic luminescence assay; (author manuscript; 17 pgs.) Analytical Biochemistry; 429(1); pp. 11-17; Oct. 2012.

Svoboda et al.; Cation exchange membrane integrated into a microfluidic device; Microelectronic Engineering; 86; pp. 1371-1374; Apr-Jun. 2009.

Szarewski et al.; Contraception. Current state of the art. British Medical Journal, 302(6787), pp. 1224-1226, May 1991.

Szymczak et al.; Concentration of Sex Steroids in Adipose Tissue after Menopause. Steroids, 63(5-6), pp. 319-321, May/Jun. 1998.

Tachibana et al.; Application of an enzyme chip to the microquantification of L-phenylalanine, Analytical Biochemistry, 359(1), pp. 72-78, Dec. 2006.

Tan et al.; A lab-on-a-chip for detection of nerve agent sarin in blood; Lab Chip; 8(6); pp. 885-891; Jun. 2008.

Tecan; Freedom EVO; 16 pages; retrieved from the internet: https (//instruments.cz/wp-content/uploads/2018/04/EVO.pdf) Oct. 4, 2023.

Teh et al.; Droplet microfluidics, Lab Chip, 8(2), pp. 198-220, Feb. 2008.

Theberge et al.; Microdroplets in microfluidics: an evolving plarform for discoveries in chemistry and biology; Angewandte Chemie International Edition; 49(34); pp. 5846-5868; Aug. 2010.

Therrell et al.; Newborn screening in North America, Journal of Inherited Metabolic Disease, 30(4), pp. 447-465, Aug. 2007.

Tian et al., Printed two-dimensional micro-zone plates for chemical analysis and ELISA, Lab on a Chip, 11(17), pp. 2869-2875, Sep. 2011.

Tobjörk et al., IR-sintering of ink-jet printed metal-nanoparticles on paper, Thin Solid Films, 520(7), pp. 2949-2955, Jan. 2012.

Tomita et al.; Loop-mediated isothermal amplification (LAMP) of gene sequences and simple visual detection of products; Nature Protocols; 3(5); pp. 877-882; (online) Apr. 2008.

Torkkeli; Droplet microfluidics on a planar surface; VTT Technical Research Centre of Finland; Publications 504; 214 pages (Dissertation); Oct. 2003.

Turgeon et al.; Combined Newborn Screening for Succinylacetone, Amino Acids, and Acylcarnitines in Dried Blood Spots, Clinical Chemistry, 54(4), pp. 657-664, Apr. 2008.

Udenfriend et al.; Fluorescamine: a reagent for assay of amino acids, peptides, proteins, and primary amines in the picomole range, Science, 178(4063), pp. 871-872, Nov. 1972.

Unger et al.; Monolithic microfabricated valves and pumps by multilayer soft lithography, Science, 288(5463), pp. 113-116, Apr. 2000.

Univ. of Maryland—Baltimore Washington Medical Center; Plasma amino acids, 6 pgs., retrieved Feb. 10, 17 from: http://www.mybwmc.org/library/1/003361, Web address available to applicant(s) at least as of Jan. 2010.

Verkman; Drug Discovery In Academia; Am J Physiol Cell Physiol; 286(3); pp. C465-C474; Feb. 2004.

Walker et al.; A Chemiluminescent DNA Probe Test Based on Strand Displacement Amplification (Chapter 15); Molecular Methods for Virus Detection (1st Ed.), Academic Press, Inc., pp. 329-349; Jan. 1995.

Walker et al.; A passive pumping method for microfluidic devices, Lab Chip, 2(3), pp. 131-134, Aug. 2002.

Wang et al., Paper-based chemiluminescence ELISA: lab-on-paper based on chitosan modified paper device and, Biosens. Bioelectron., 31(1), pp. 212-218, Jan. 2012.

Wang et al., Simple and covalent fabrication of a paper device and its application in sensitive chemiluminescence immunoassay, Analyst, 137(16), pp. 3821-3827, Aug. 2012.

Wang et al.; An integrated microfluidic device for large-scale in situ click chemistry screening; Lab on a Chip; 9(16); 9(16); pp. 2281-2285; 9 pages (Author Manuscript); Aug. 2009.

Wang et al.; Highly sensitive detection of microRNAs based on isothermal exponential amplification-assisted generation of catalytic G-quadruplexDNAzyme; Biosensors and Bioelectronics, 42; pp. 131-135; Apr. 2013.

Washburn et al.; Large-scale analysis of the yeast proteome by multidimensional protein identification technology, Nat. Biotechnol., 19(3), pp. 242-247, Mar. 2001.

(56) References Cited

OTHER PUBLICATIONS

Watson et al.; Multilayer hybrid microfluidics: a digital-to-channel interface for sample processing and separations; Anal. Chem.; 82(15); pp. 6680-6686; Aug. 2010.

Wheeler et al.; Electrowetting-Based Microfluidics for Analysis of Peptides and Proteins by Matrix-Assisted Laser Desorption/Ionization Mass Spectrometry; Anal Chem; 76(16); pp. 4833-4838; Aug. 2004.

Wheeler; Chemistry. Putting electrowetting to work; Science; 322(5901); pp. 539-540; Oct. 2008.

Wlodkowic et al.; Tumors on chips: oncology meets microfluidics; Current opinion in Chemical Biology; 14(5); pp. 556-567; Oct. 2010.

Wu et al.; Design, Simulation and Fabrication of Electrowetting-Based Actuators for Integrated Digital Microfluidics; Proceedings of the 1st IEEE International Conference on Nano/Micro Engineered and Molecular Systems; Zhuhai, China; pp. 1097-1100; Jan. 18-21, 2006.

Wu et al.; Electrophoretic separations on microfluidic chips, J. Chromatogr. A, 1184(1-2), pp. 542-559, Mar. 2008.

Yan et al., A microfluidic origami electrochemiluminescence aptamer-device based on a porous Au-paper electrode and a phenyleneethynylene derivative, Chem. Commun. (Camb), 49(14), pp. 1383-1385, Feb. 2013.

Yan et al., Paper-based electrochemiluminescent 3D immunodevice for lab-on-paper, specific, and sensitive point-of-care testing, Chem.—Eur. J., 18(16), pp. 4938-4945, Apr. 2012.

Yi et al.; Spangler et al., Eds; Channel-to-droplet extractions for on-chip sample preparation, in Proceedings of Solid-State Sensor, Actuator and Microsystems Workshop, pp. 128-131, Jun. 2006.

Yin et al.; One-step, multiplexed fluorescence detection of microRNAs based on duplex-specific nuclease signal amplification; J. American Chem. Soc.; 134(11); pp. 5064-5067; Mar. 2012.

Yoon et al.; Preventing Biomolecular Adsorption in Electrowetting-Based Biofluidic Chips; Anal Chem; 75; pp. 5097-5102; Aug. 2003.

Yoon; Open-Surface Digital Microfluidics; The Open Biotechnology Journal; 2(1); pp. 94-100; Apr. 2008.

Young et al.; Calculation of DEP and EWOD Forces for Application in Digital Microfluidics, J. Fluids Eng., 130(8), pp. 081603-1-081603-9, Jul. 2008.

Yu et al., Monolithic porous polymer for on-chip solid-phase extraction and preconcentration prepared by photoinitiated in situ polymerization within a microfluidic device, Analytical Chemistry , 73(21), pp. 5088-5096, Nov. 2001.

Yu et al., Preparation of monolithic polymers with controlled porous properties for microfluidic chip applications using photoinitiated free-radical polymerization, Journal of Polymer Science, Part A: Polymer Chemistry, 40(6), pp. 755-769, Mar. 2002.

Yu et al.; A plate reader-compatible microchannel array for cell biology assays; Lab Chip; 7(3); pp. 388-391; Mar. 2007.

Yu et al.; Microfabrication of a digital microfluidic platform integrated with an on-chip electrochemical cell; Journal of Micromechanics and Microengineering; 23(9); pp. 10 pages; doi: 10.1088/0960-1317/23/9/095025; Aug. 2013.

Yu et al.; Parallel-plate lab-on-chip electrochemical analysis; Journal of Micromechanics and Microengineering; 24(1); 7 pages; doi: 10.1088/0960-1317/24/1/015020; Dec. 16, 2013.

Yue; Undergraduate Chemistry experiment (11); Hunan Normal University Press; First Edition; p. 96; (Machine Translation included); Oct. 2008.

Yung et al.; Micromagnetic-microfluidic blood cleansing devices; Lab on a Chip; 9(9); pp. 1171-1177; May 2009.

Zaffanello et al.; Multiple positive results during a neonatal screening program: a retrospective analysis of incidence, clinical implications and outcomes, Journal of Perinatal Medicine, 33(3), pp. 246-251, May 2005.

Zhang et al.; Multiplexed detection of microRNAs by tuning DNA-scaffolded silver nanoclusters; Analyst; 138(17); pp. 4812-4817; Sep. 2013.

Zhang et al.; The permeability characteristics of silicone rubber; In Proceedings of 2006 SAMPE Fall Technical Conference; 10 pages; Nov. 6, 2006.

Zhao et al., Lab on Paper, Lab Chip, 8(12), pp. 1988-1991, Dec. 2008.

Znidarsic-Plazl et al.; Steroid extraction in a microchannel system—mathematical modelling and experiments. Lab Chip, 7(7), pp. 883-889, Jul. 2007.

Zuker; Mfold Web Server for Nucleic Acid Folding and Hybridization Prediction; Nucleic Acid Research ; 31(13); pp. 3406-3415; Jul. 2003.

Zytkovicz et al.; Tandem mass spectrometric analysis for amino, organic, and fatty acid disorders in newborn dried blood spots: a two-year summary from the New England Newborn Screening Program, Clinical Chemistry, 47(11), pp. 1945-1955, Nov. 2001.

Jebrail et al.; U.S. Appl. No. 18/451,828 entitled "Methods of mechanical microfluidic manipulation," filed Aug. 17, 2023.

Jebrail et al.; U.S. Appl. No. 18/568,534 entitled "Apparatuses and methods for digital microfluidics and micro-electroporation," filed Dec. 8, 2023.

Jebrail et al.; U.S. Appl. No. 18/402,701 entitled "Sequencing by synthesis using mechanical compression," filed Jan. 2, 2024.

Jebrail et al.; U.S. Appl. No. 18/416,693 entitled "Evaporation management in digital microfluidic devices," filed Jan. 18, 2024.

Chemical Book; Paraffin Wax; 2 pages; retrieved from the internet (https://www.chemicalbook.com/ChemicalProductProperty_EN_CB2854418.htm) on May 16, 2024.

merriam-webster.com; Replenish (definition); 11 pages; retrieved from the internet (https://www.merriam-webster.com/dictionary/replenish) on Jul. 22, 2024.

Jebrail et al.; U.S. Appl. No. 18/642,774 entitled "Control of evaporation in digital microfluidics," filed Apr. 22, 2024.

Jebrail et al.; U.S. Appl. No. 18/766,551 entitled "Microfluidic two-dimensional capillary manipulation devices and methods," filed Jul. 8, 2024.

\* cited by examiner

SIDE VIEW
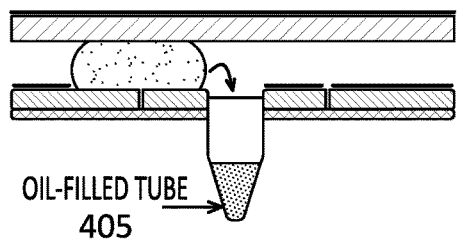
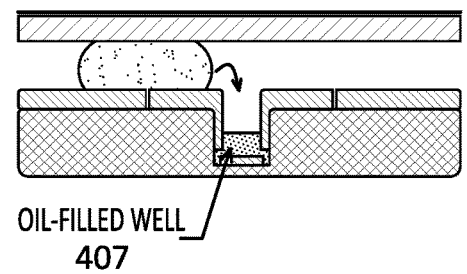
FIG. 4A
FIG. 4B

AIR-MATRIX DIGITAL MICROFLUIDICS APPARATUSES AND METHODS FOR LIMITING EVAPORATION AND SURFACE FOULING

CROSS REFERENCE TO RELATED APPLICATIONS

This application is a continuation of U.S. patent application Ser. No. 17/405,800, filed Aug. 18, 2021, entitled "AIR-MATRIX DIGITAL MICROFLUIDICS APPARATUSES AND METHODS FOR LIMITING EVAPORATION AND SURFACE FOULING," now U.S. Patent No. 11,944,974, which is a continuation of U.S. application Ser. No. 16/523,876, filed Jul. 26, 2019, entitled "AIR-MATRIX DIGITAL MICROFLUIDICS APPARATUSES AND METHODS FOR LIMITING EVAPORATION AND SURFACE FOULING," now U.S. Pat. No. 11,097,276, which is a continuation of U.S. patent application Ser. No. 15/579,455, filed Dec. 4, 2017, now U.S. Pat. No. 10,464,067, which is a national phase of International Application No. PCT/US2016/036015, filed Jun. 6, 2016 entitled "AIR-MATRIX DIGITAL MICROFLUIDICS APPARATUSES AND METHODS FOR LIMITING EVAPORATION AND SURFACE FOULING," now International Publication No. WO 2016/197103, which claims priority to U.S. Provisional Patent Application No. 62/171,756, filed Jun. 5, 2015, entitled "DEVICE AND METHODS FOR LIMITING EVAPORATION AND SURFACE FOULING," all of which are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Air-matrix digital microfluidic (DMF) apparatuses and methods that limit or prevent evaporation and/or surface fouling are described herein.

BACKGROUND

Microfluidics has come a long way to transform the way traditional procedures in molecular biology, medical diagnostics, and drug discovery are performed. Lab-on-a-chip and biochip type devices have drawn much interest in both scientific research applications as well as potentially for point-of-care applications because they carryout highly repetitive reaction steps with a small reaction volume, saving both materials and time. While traditional biochip-type devices utilize micro- or nano-sized channels and typically require corresponding micropumps, microvalves, and microchannels coupled to the biochip to manipulate the reaction steps, these additional components greatly increase cost and complexity of the microfluidic device.

Digital microfluidics (DMF) has emerged as a powerful preparative technique for a broad range of biological and chemical applications. DMF enables real-time, precise, and highly flexible control over multiple samples and reagents, including solids, liquids, and even harsh chemicals, without need for pumps, valves, or complex arrays of tubing. In DMF, discrete droplets of nanoliter to microliter volumes are dispensed from onto a planar surface coated with a hydrophobic insulator, where they are manipulated (transported, split, merged, mixed) by applying a series of electrical potentials to an embedded array of electrodes. Complex reaction steps can be carried out using DMF alone, or using hybrid systems in which DMF is integrated with channel-based microfluidics.

Despite significant advances, both evaporation, particularly in air-matrix DMF, and surface fouling remains issues. Surface fouling occur when components from the reaction mixture irreversibly adheres to surfaces of the microfluidic or DMF device after contacting these surfaces. Surface fouling is a particularly acute problem when operating a higher (e.g., greater than 37° C.) temperatures. Various strategies have been proposed to prevent surface fouling, such as using polymers, glass, and metals to fabricate the microfluidic channels or chemical modification of material surfaces. However, these strategies have had limited success, particularly in the context of DMF, despite efforts to test and fabricate surfaces and surface coatings that are resistant to surface fouling. In some instances, a coating intended to prevent surface fouling may cause undesirable interactions and secondary reactions with the reaction mixture and/or reagents used. In general, it would be desirable to have a simple solution to minimizing surface fouling in microfluidic and DMF devices.

Evaporation is also a concern when performing reactions in an air-matrix DMF device. In general, an air-matrix DMF apparatus may refer to any non-liquid interface of the DMF apparatus in which the liquid droplet being manipulated by the DMF apparatus is surrounded by an air (or any other gas) matrix. As used herein, an air-matrix may also and interchangeably be referred to as a "gas-matrix" DMF apparatus; the gas does not have to be air, though it may be. Evaporation may be especially problematic in air-matrix DMF methods and that heat for a prolonged period of time (e.g., greater than 30 seconds). Evaporation limits the utility of air-matrix DMF, because enzymatic reactions are often highly sensitive to changes in reactant concentration. Largely for this reason, others have attempted to use oil-matrix DMF for biochemical applications, despite numerous drawbacks including: the added complexity of incorporating gaskets or fabricated structures to contain the oil; unwanted liquid-liquid extraction of reactants into the surrounding oil; incompatibility with oil-miscible liquids (e.g., organic solvents such as alcohols); and efficient dissipation of heat, which undermines localized heating and often confounds temperature-sensitive reactions. Another strategy for addressing evaporation has been to place the air-matrix DMF device in a closed humidified chamber, but this often results in unwanted condensation on the DMF surface, difficult and/or limited access to the device, and a need for additional laboratory space and infrastructure.

It has also been proposed to address evaporation by transferring reaction droplets from the air-matrix DMF device to microcapillaries, where they can be heated in dedicated off-chip modules without evaporation problems. However, this complicates design and manufacture of the air-matrix DMF device, and introduces the added complications of microcapillary interfaces and coordination with peripheral modules.

Thus, there exists a need for air-matrix DMF apparatuses and methods that may prevent or limit evaporation and/or prevent or limit surface fouling. Described herein are apparatuses and methods that may address this need.

SUMMARY OF THE DISCLOSURE

Described herein are air-matrix DMF apparatuses that minimize surface fouling and/or evaporation.

A typical DMF apparatus may include parallel plates separated by an air gap; one of the plates (typically the bottom plate) may contain a patterned array of individually controllable actuation electrodes, and the opposite plate (e.g., the top plate) may include one or more ground electrode. Alternatively, the one or more ground electrode(s) can be provided on the same plate as the actuating (e.g., high-voltage) electrodes. The surfaces of the plates in the air gap may include a hydrophobic material which may be dielectric or in some variations an additional dielectric layer may be included. The hydrophobic and/or dielectric layer(s) may decrease the wettability of the surface and add capacitance between the droplet and the control electrode. Droplets may be moved or otherwise manipulated while in the air gap space between the plates. The air gap may be divided up into regions, and some regions of the plates may include heating/cooling by a thermal regulator (e.g., a Peltier device, a resistive heating device, a convective heating/cooling device, etc.) that is in thermal contact with the region, and may be localized to that region. Reactions performed on with the air-matrix DMF apparatus may be detected, including imaging or other sensor-based detection, and may be performed at one or more localized regions or over all or over a majority of the air gap space of the air-matrix DMF apparatus.

In general, any of the air-matrix apparatuses described herein may include a reaction chamber opening that extends transversely through a plate of the apparatus. The reaction chamber opening is typically configured to put a reaction chamber well in fluid communication with the air gap. The opening through the plate may be referred to as the reaction chamber opening and the chamber into which this opening exits may be referred to as the reaction chamber well (or simply 'reaction chamber'). A reaction chamber opening may be at least partially surrounded by an actuation electrode from the plurality of actuation electrodes; these electrodes may extend down into the opening, out of the plane of the plate. In any of these variations, the reaction chamber opening may pass through an actuation electrode.

A reaction chamber opening may be any appropriate size and shape. The opening may be round, oval, square, triangular, hexagonal, rectangular, etc. The reaction chamber opening may be between 0.1 mm and 20 mm wide (e.g., between 1 and 15 mm, between 2 and 12 mm, wide, etc.).

The air-matrix DMF apparatuses and methods described herein may enable facile and reliable execution of biochemical reactions over a range of temperatures (including but not limited to 4-95° C.) and incubation times (including but not limited to times up to 6 hr. or more, e.g., up to 1 hr., up to 2 hr., up to 3 hr., etc.). The air-matrix DMF apparatuses described herein may include at least one reaction chamber well, and/or may be configured to couple to one or more reaction chamber wells. The reaction chamber wells may be in close proximity to at least one actuating electrode. In some variations the reaction chamber well may include one or more actuation electrodes that are out of the plane of the plurality of actuation electrodes operation in the air gap. The reaction chamber well may be in fluid communication with other areas of the air gap region of the DMF apparatus.

The air gap region of the air matrix DMF apparatus may include one or more regions for holding starting reaction solutions as well as regions for other solutions that may include subsequent components for the reaction (e.g., enzymes, nucleotides, etc.) or additional reaction solution (solvent). One or more reservoirs may be in communication with the air gap, and in some instances there may be access holes for introducing solutions having starting material, reagent solution, and so forth. Access holes may be connected to external sources of starting components, other reaction component, reaction reagents, and so on. In other instances, the DMF apparatus may be provided having all the reaction materials needed.

A reaction chamber well may be located in close proximity to one or more actuating electrodes. For example, an actuating electrode may be in contact with the reaction chamber opening to enable transportation of a droplet into the reaction compartment. In some instances, the reaction chamber well(s) may be removable from air gap DMF apparatus; for example, the reaction chamber well may be a centrifuge tube (e.g., microcentrifuge tubes, Eppendorf tubes, etc., of any appropriate volume, such as 0.2 ml, 0.3 ml, 0.4 ml, 0.5 ml, 0.6 ml, 0.7 ml, 0.8 ml, 0.9 ml, 1 ml, 1.2 ml, 1.4 ml, 1.5 ml, 1.8 ml, 2 ml, etc.) or a multi-well plate (e.g., microtiter plates, etc. of any appropriate size and volume, such as 96 well plates, 384 well plates, 1536 well plates, etc.) that may be securely coupled to the reaction chamber opening. In some variations the reaction chamber well may be formed within either the first or second plate, such as formed of a printed circuit board (PCB) that may also act as a substrate for the actuating electrodes.

For example, described herein are air-matrix digital microfluidic (DMF) apparatuses configured to prevent evaporation and surface fouling. The air-matrix DMF apparatus may include: a first plate having a first hydrophobic layer; a second plate having a second hydrophobic layer; an air gap formed between the first and second hydrophobic layers; a plurality of actuation electrodes arranged in a first plane adjacent to the first hydrophobic layer; one or more ground electrodes; and a reaction chamber opening that extends transversely through the first plate, the reaction chamber opening configured to put a reaction chamber well in fluid communication with the air gap, wherein the reaction chamber opening is at least partially surrounded by an actuation electrode from the plurality of actuation electrodes.

An air-matrix digital microfluidic (DMF) apparatus configured to prevent evaporation and surface fouling may include: a first plate having a first hydrophobic layer; a second plate having a second hydrophobic layer; an air gap formed between the first and second hydrophobic layers; a plurality of actuation electrodes arranged in a first plane adjacent to the first hydrophobic layer; one or more ground electrodes; a reaction chamber opening that extends through first plate, the reaction chamber opening configured to put a reaction chamber well in fluid communication with the air gap, wherein the reaction chamber opening is at least partially surrounded by an actuation electrode from the plurality of actuation electrodes; a reaction chamber cover adjacent to the reaction chamber opening, the reaction chamber cover configured to be actuated to close over the reaction chamber opening and separate the reaction chamber from the air gap; and a controller electrically coupled to the plurality of actuation electrodes and configured to apply energy to the plurality of actuation electrodes to move a droplet into and out of the reaction chamber. An air-matrix digital microfluidic (DMF) apparatus configured to prevent evaporation and surface fouling may include: a first plate having a first hydrophobic layer; a second plate having a second hydrophobic layer; an air gap formed between the first and second hydrophobic layers; a plurality of actuation electrodes arranged in a first plane adjacent to the first hydrophobic layer; one or more ground electrodes; a reaction chamber opening that extends through the first plate transverse to the first plane, the reaction chamber opening configured to put a reaction chamber well in fluid communication with the air gap, wherein the reaction chamber opening is at least partially surrounded by an actuation electrode from the plurality of actuation electrodes; one or more reaction chamber actuation electrodes within the reaction chamber opening, wherein the one or more reaction chamber actuation electrodes are positioned or extend out of the first plane; a reaction chamber cover adjacent to the reaction chamber opening, the reaction chamber cover configured to be actuated to close over the reaction chamber opening and separate the reaction chamber from the air gap; and a controller electrically coupled to the plurality of actuation electrodes and the one or more reaction chamber actuation electrodes and configured to apply energy to move a droplet into and out of the reaction chamber.

Any of these apparatuses may include a reaction chamber cover. In general, the term 'cover' is broadly understood to be any cover, including a cover configured to close off the reaction chamber from the air gap, and/or sealing the reaction chamber, and one or more substances in the reaction chamber (e.g., oil, wax, etc.) that cover the reaction droplet when it is within the reaction chamber well.

In some variations the reaction chamber cover is positioned adjacent to the reaction chamber opening, and is configured to be actuated to close over the reaction chamber opening and separate the reaction chamber from the air gap.

Any of the apparatus variations described herein may include oil or wax within the reaction chamber. As described herein, wax may be included in the air gap even if a separate reaction chamber apparatus is included. The wax may be present in a thermal zone (e.g., a thermally controlled sub-region of the air gap) as a solid (e.g., a wall, channel, cave, or other structure of wax) that can be melted to form a liquid and combined with a reaction droplet. The liquid wax, upon mixing together with the reaction droplet, will typically form a coating over and around the liquid droplet, protecting it from evaporation.

The reaction chamber opening may be surrounded and pass through an actuation electrode from the plurality of actuation electrodes. For example, a reaction chamber opening may be a hole through an actuation electrode and any other layers of a plate. Any of the reaction wells described herein may also or alternatively include one or more reaction chamber actuation electrodes within the reaction chamber opening. The reaction chamber activation electrodes may be configured to connect to the same controller controlling and/or coordinating activation of the plurality of actuation electrodes, e.g., to move one or more droplets within the air gap. For example, the DMF apparatus may include one or more reaction chamber actuation electrodes within the reaction chamber opening, wherein the one or more reaction chamber actuation electrodes are positioned out of the first plane. The DMF apparatus may also or alternatively include one or more reaction chamber actuation electrodes within the reaction chamber opening, wherein the one or more reaction chamber actuation electrodes are positioned within the reaction chamber. All or a part of the reaction chamber well may include an outer hydrophobic surface. For example, the outer surface may be coated with a hydrophobic coating layer (which may also be a dielectric material/coating). In some variations, just the region over (immediately adjacent to) the actuation electrodes is hydrophobic; for example the reaction chamber activation electrodes may be coated with a dielectric and hydrophobic coating.

The reaction chamber cover may be coupled to the second plate. For example, when the reaction chamber cover includes a plastic, metal or other foreign material that is adapted (e.g., sized, shaped, etc.) to fit into the reaction chamber opening, and in some cases seal it off. The second plate may be flexible and configured to be pushed to seal the reaction chamber cover over the reaction chamber opening. In some variation the second plate is itself acts as a reaction chamber lid, deflecting to close off the reaction chamber opening. In general, the second plate may be flexible and configured to be pushed to seal over the reaction chamber opening.

Any of the air matrix DMF apparatuses described herein may include a thermal regulator adjacent to the first plate and configured to control the temperature of a portion of the air gap and the reaction chamber.

As mentioned above, the air matrix DMF may include any appropriate reaction chamber wells that form part of or are connected to a plate of the apparatus. For example, a reaction chamber well may be formed within a thickness of the plate (e.g., within a substrate such as the PCB forming a plate). Thus, the first plate may comprise a reaction chamber within a thickness of the first plate. The first plate may include a printed circuit board (PCB) and the reaction chamber is formed as a well within the PCB. Alternatively, the air-matrix DMF apparatus may include a first plate that is configured to mate with a multi-well plate so that the reaction chamber opening mates with a well of the multi-well plate. Alternatively or additionally, the DMF apparatus's first plate may be configured to mate with a centrifuge tube so that the reaction chamber opening mates with the centrifuge tube.

The air gap layer may generally include at least one sample region and at least one reagent region.

In any of the variations described herein, the reaction chamber opening may be flush with the hydrophobic layer and/or dielectric layer. The reaction chamber well's internal surface may be hydrophilic or hydrophobic. For example, in variations in which there are no actuating electrodes in the reaction chamber well (that may actively move a droplet into a well), it may be beneficial that the surface be hydrophilic to attract the droplet and pull it inside the well. In variations in which there are one or more actuating electrodes in the reaction chamber well, the surface may be hydrophobic. As mentioned, any of the reaction chamber wells (which may be referred to herein as just 'reaction chambers' for simplicity) may include one or more electrode, e.g., actuation electrodes.

Also described herein are methods of preventing or reducing evaporation using an air gap DMF apparatus. For example, a method of operating a matrix digital microfluidic (DMF) apparatus to prevent evaporation and surface fouling may include: introducing a reaction droplet into an air gap of the air-matrix DMF apparatus which is formed between a first plate and a second plate of the air-matrix DMF apparatus; transporting the reaction droplet along the air gap and through a reaction chamber opening that extends through the first plate, and into a reaction chamber well; covering the reaction droplet within the reaction chamber well to protect the reaction droplet from evaporation; and allowing a reaction to proceed within the reaction droplet.

A method of operating a matrix digital microfluidic (DMF) apparatus to prevent evaporation and surface fouling may include: introducing a reaction droplet into an air gap of the air-matrix DMF apparatus which is formed between a first plate and a second plate of the air-matrix DMF apparatus, wherein the first plate comprises a plurality of adjacent actuation electrodes; transporting the reaction droplet along the air gap and through a reaction chamber opening that extends through the first plate, and into a reaction chamber well by applying energy to a subset of the actuation electrodes of the plurality of actuation electrodes; covering the reaction droplet within the reaction chamber well to protect the reaction droplet from evaporation; and heating the reaction chamber well so that a reaction may proceed within the reaction droplet.

A method of operating a matrix digital microfluidic (DMF) apparatus to prevent evaporation and surface fouling may include: introducing a reaction droplet into an air gap of the air-matrix DMF apparatus which is formed between a first plate and a second plate of the air-matrix DMF apparatus, wherein the first plate comprises a plurality of adjacent actuation electrodes; transporting the reaction droplet along the air gap and through a reaction chamber opening that extends through the first plate, and into a reaction chamber well by applying energy to a subset of the actuation electrodes of the plurality of actuation electrodes; sealing the reaction chamber well opening with a cover to close off the reaction chamber opening from the air gap to protect the reaction droplet from evaporation; and heating the reaction chamber well so that a reaction may proceed within the reaction droplet.

Introducing the reaction droplet into an air gap may generally include combining multiple droplets to form a reaction droplet within the air gap.

In any of these examples, the first plate may include a plurality of adjacent actuation electrodes, and wherein transporting the reaction droplet comprises applying energy to a subset of the actuation electrodes of the plurality of adjacent actuation electrodes. In any of these examples, covering the reaction droplet may include sealing the reaction chamber well opening with a cover to close off the reaction chamber opening from the air gap to protect the reaction droplet from evaporation.

Covering the reaction chamber may generally comprise combining the reaction droplet with a droplet of oil or wax within the reaction chamber. As mentioned, the oil or wax may mix with the reaction droplet and enclose it, protecting it from evaporation. The droplet may still be visualized through the cover, including any wax or oil cover formed by combining with a reaction droplet.

In any of the variations described herein, allowing a reaction to proceed may comprise heating the reaction chamber well, e.g., using the same or a different thermal controller than described previously for heating and/or cooling the thermal zone.

In some variations, sealing the reaction chamber well opening comprises pushing on the second plate to cover the reaction chamber well opening.

Any of these methods may also include moving the reaction chamber droplet from the reaction well and into the air gap by applying energy to at least one actuation electrode within the reaction well. Any of these methods may also include detecting a product within the reaction droplet. The product may be detected visually and/or (e.g., using a colorimetric test, etc.) or like.

Also described herein are air-matrix DMF apparatuses that include a wax material in a solid state at room temperature and below, but may selectively and controllably combined with a reaction droplet within the air gap when the wax structure is heated. For example, described herein are air-matrix digital microfluidic (DMF) apparatuses configured to prevent evaporation. The apparatus may include a first plate having a first hydrophobic layer; a second plate having a second hydrophobic layer; an air gap formed between the first and second hydrophobic layers; a plurality of actuation electrodes adjacent to the first hydrophobic layer, wherein each actuation electrode defines a unit cell within the air gap; one or more ground electrodes adjacent to actuation electrode of the plurality of actuation electrodes; a thermal regulator arranged to heat a thermal zone portion of the air gap wherein a plurality of unit cells are adjacent to the thermal zone; a wax body within the thermal zone of the air gap; and a controller configured to regulate the temperature of the thermal zone to melt the wax body and to apply energy to actuation electrodes of the plurality of actuation electrode to move a droplet through the air gap.

The wax body may span one or more (e.g., a plurality of adjacent) unit cells. The wax body may comprise a wall of wax within the air gap. In some variations the wax body forms a channel or vessel within the air gap. For example, the wax body may form a concave shape in the air gap, which may help it combine with a reaction droplet when heated. In general, the wax body may be melted immediately before combining with the reaction droplet. In some variations the wax body may itself be a droplet (wax droplet) that is moved into position by the air-matrix DMF apparatus so that it can combine with the reaction droplet.

The wax body may be formed of any appropriate wax that is typically solid at room temperature, such as, e.g., paraffin wax. Other waxes may generally include hydrophobic, malleable solids near ambient temperatures such as higher alkanes and lipids, typically with melting points above about 40° C. (104° F.), that may melt to give low viscosity liquids. Examples of waxes include natural waxes (beeswax, plant waxes, petroleum waxes, etc.).

Any of these apparatuses may include features such as those described above, e.g., at least one temperature sensor in thermal communication with the thermal regulator. The plurality of actuation electrodes may form a portion of the first plate. The one or more ground electrodes may be adjacent to the second hydrophobic layer, across the air gap from the first plate. The apparatus may also include a dielectric between the first hydrophobic layer and the plurality of actuation electrodes (or in some variations the dielectric layer is the hydrophobic layer, as some hydrophobic layers are also dielectric materials). As mentioned above, a thermal regulator may be a thermoelectric heater.

Also described herein are methods of preventing droplet evaporation within an air-matrix digital microfluidic (DMF) apparatus, the method may include: introducing a reaction droplet into an air gap of the air-matrix DMF apparatus which is formed between a first plate and a second plate of the air-matrix DMF apparatus; melting a wax body within the air gap of the air-matrix DMF; combining the reaction droplet with the melted wax body to protect the reaction droplet from evaporation; and allowing a reaction to proceed within the reaction droplet.

Melting the wax body typically comprises increasing the temperature of a portion of the air gap comprising a thermal zone to a temperature above the melting point of the wax forming the wax body. In some variations, melting the wax body comprises melting a solid wax body formed into a wall or open chamber within the air gap.

Introducing the reaction droplet into an air gap may comprise combining multiple droplets to form a reaction droplet within the air gap. The first plate may comprise a plurality of adjacent actuation electrodes, and wherein combining the reaction droplet with the melted wax body comprises applying energy to a subset of the actuation electrodes of the plurality of adjacent actuation electrodes to move the reaction droplet in contact with the wax body prior to melting the wax body.

The first plate may comprise a plurality of adjacent actuation electrodes, wherein combining the reaction droplet with the melted wax body may comprise applying energy to a subset of the actuation electrodes of the plurality of adjacent actuation electrodes to move the reaction droplet in contact with the melted wax body.

Allowing a reaction to proceed may comprise heating portion of the air gap containing the reaction droplet. As mentioned, any of these methods may include detecting a product within the reaction droplet.

Although the majority of the devices described herein are air-matrix DMF apparatuses that include two parallel pates forming the air gap, any of the techniques (methods and apparatuses) may be adapted for operation as part of a one-plate air-matrix DMF apparatus. In this case, the apparatus includes a single plate and may be open to the air above the single (e.g., first) plate; the "air gap" may correspond to the region above the plate in which one or more droplet may travel while on the single plate. The ground electrode(s) may be positioned adjacent to (e.g., next to) each actuation electrode, e.g., in, on, or below the single plate. The plate may be coated with the hydrophobic layer (and an additional dielectric layer maybe positioned between the hydrophobic layer and the dielectric layer, or the same layer may be both dielectric and hydrophobic). The methods and apparatuses for correcting for evaporation may be particularly well suited for such single-plate air-matrix DMF apparatuses.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4A and 4B show side views of air-matrix DMF apparatuses in which a reaction chamber well includes an inert coating substance (e.g., oil, wax, etc.) that may combine with and cover the reaction droplet.

FIG. 5A shows the reaction chamber well (configured as a tube) before the reaction chamber opening is sealed, and FIG. 5B shows the reaction chamber well after pushing on the flexible top plate to seal the reaction chamber opening with the plug.

FIG. 5C shows the reaction chamber well before it is scaled and FIG. 5D shows the reaction chamber well after pushing down on the top plate to seal it.

DETAILED DESCRIPTION

Figure 1:
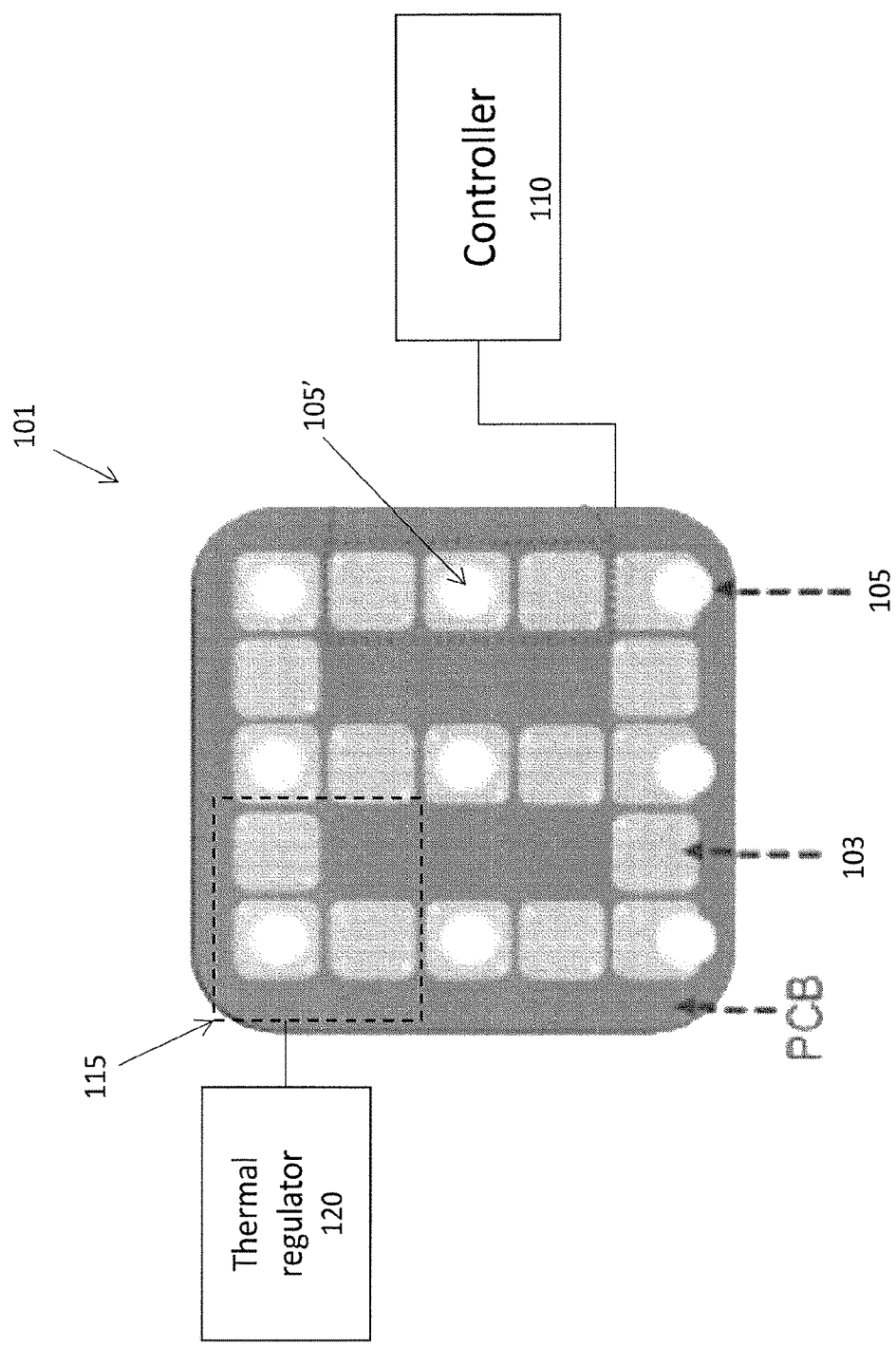
FIG. 1 is a top view of an example of a portion of an air-matrix DMF apparatus, showing a plurality of unit cells (defined by the underlying actuating electrodes) and reaction chamber openings (access holes).

Described herein are air-matrix digital microfluidics (DMF) methods and apparatuses that may minimize the effect of surface fouling and/or evaporation. An air-matrix DMF apparatus as described herein may be particularly useful when heating the reaction droplets being processed.

In general, an air-matrix DMF apparatus as disclosed herein may have any appropriate shape or size. As used herein, the term "surface fouling" may refer to accumulation of unwanted materials on solid surfaces, including with the air gap of the air matrix DMF apparatus (e.g., upper and/or lower plate surfaces). Surface fouling materials can consist of either living organisms (biofouling) or a non-living substance (inorganic or organic). Surface fouling is usually distinguished from other surface-growth phenomena in that it occurs on a surface of a component, or system and that the fouling process impedes or interferes with function.

The air-matrix DMF apparatuses described herein generally include at least one hydrophobic surface and a plurality of activation electrodes adjacent to the surface; either the hydrophobic surface may also be a dielectric material or an additional dielectric material/layer may be positioned between the actuation electrodes and the hydrophobic surface. For example, in some variations, the air-matrix DMF includes a series of layers on a printed circuit board (PCB) forming a first or bottom plate. The outer (top) surface of this plate is the hydrophobic layer. Above this layer is the air gap (air gap region) along which a reaction droplet may be manipulated. In some variations a second plate may be positioned opposite from the first plate, forming the air gap region between the two. The second plate may also include a hydrophobic coating and in some variations may also include a ground electrode or multiple ground electrodes opposite the actuation electrodes. The actuation electrodes may be configured for moving droplets from one region to another within the DMF device, and may be electrically coupled to a controller (e.g., control circuitry) for applying energy to drive movement of the droplets in the air gap. As mentioned, this plate may also include a dielectric layer for increasing the capacitance between the reaction droplet and the actuation electrodes. The reaction starting materials and reagents, as well as additional additive reagents may be in reservoirs that may be dispensed into the air gap, where the reaction mixture is typically held during the reaction. In some instances the starting materials, reagents, and components needed in subsequent steps may be stored in separate areas of the air gap layer such that their proximity from each other prevents them from prematurely mixing with each other. In other instances, the air gap layer may include features that are able to compartmentalize different reaction mixtures such that they may be close in proximity to each other but separated by a physical barrier. In general, the floor of the air gap is in the first plate, and is in electrical contact with a series of actuation electrodes.

The air gap DMF apparatuses described herein may also include other elements for providing the needed reaction conditions. For instance, the air gap DMF apparatuses may include one or more thermal regulators (e.g., heating or cooling element such as thermoelectric modules) for heating and cooling all or a region (thermal zone) of the air gap. In other instances, heating or cooling may be provided by controlling endothermic or exothermic reactions to regulate temperature. The air gap DMF apparatuses may also include temperature detectors (e.g. resistive temperature detector) for monitoring the temperature during a reaction run.

Thus, the air gap DMF apparatuses described herein may include one or more thermal zones. Thermal zones are regions on the air gap DMF apparatuses (e.g., the air gap) that may be heated or cooled, where the thermal zones may transfer the heating or cooling to a droplet within the thermal zone through one or more surfaces in contact with the air gap region in the zone (e.g., the first plate). Heating and cooling may be through a thermal regulator such as a thermoelectric module or other type of temperature-modulating component. The temperature of one or many thermal zones may be monitored through a temperature detector or sensor, where the temperature information may be communicated to a computer or other telecommunication device. The temperature is typically regulated between 4° C. and 100° C., as when these apparatuses are configured to perform one or more reactions such as, but not limited to: nucleic acid amplifications, like LAMP, PCR, molecular assays, cDNA synthesis, organic synthesis, etc.

An air gap DMF apparatus may also include one or more thermal voids. Thermal voids may be disposed adjacent to the different thermal zones. The thermal voids are typically regions in which heat conduction is limited, e.g., by removing part of the plate (e.g., first plate) (forming the "void"). These voids may be strategically placed to isolate one thermal zone from another which allows the correct temperatures to be maintained within each thermal zone.

In general, any of the air-matrix DMF apparatuses described herein may include a separate reaction chamber that is separate or separable from the air gap of the apparatus, but may be accessed through the air gap region. The reaction chamber typically includes a reaction chamber opening that is continuous with the lower surface of the air gap (e.g., the first plate), and a reaction chamber well that forms a cup-like region in which a droplet may be controllably placed (and in some variations, removed) by the apparatus to perform a reaction when covered. The cover may be a mechanical cover (e.g., a cover the seals or partially seals the reaction chamber opening, or a cover that encapsulates, encloses or otherwise surrounds the reaction droplet, such as an oil or wax material that mixes with (then separates from and surrounds) the reaction droplet when the two are combined in the reaction chamber.

In general, the reaction chamber opening may be any shape or size (e.g., round, square, rectangular, hexagonal, octagonal, etc.) and may pass through the first (e.g., lower) plate, and into the reaction chamber well. In some variations, the reaction chamber opening passes through one or more actuation electrodes; in particular, the reaction chamber opening may be completely or partially surrounded by an actuation electrode.

FIG. 1 shows a top view of an exemplary air-matrix DMF apparatus 101. As shown, the DMF device may include a series of paths defined by actuation electrodes. The actuation electrodes 103 are shown in FIG. 1 as a series of squares, each defining a unit cell. These actuation electrodes may have any appropriate shape and size, and are not limited to squares. For example, the unit cells formed by the actuation electrodes in the first layer may be round, hexagonal, triangular, rectangular, octagonal, parallelogram-shaped, etc. In the example of FIG. 1, the squares representing the unit cells may indicate the physical location of the actuation electrodes in the DMF device or may indicate the area where the actuation electrode has an effect (e.g., an effective area such that when a droplet is situated over the denoted area, the corresponding actuation electrode may affect the droplet's movement or other physical property). The actuation electrodes 103 may be placed in any pattern. In some examples, actuation electrodes may span the entire corresponding bottom or top surface the air gap of the DMF apparatus. The actuation electrodes may be in electrical contact with starting sample chambers (not shown) as well as reagent chambers (not shown) for moving different droplets to different regions within the air gap to be mixed with reagent droplets or heated.

In the air-matrix apparatuses described herein, the first (lower) plate also includes one or more reaction chamber openings (access holes) 105, 105'. Access to the reaction chamber wells may allow reaction droplets to be initially introduced or for allowing reagent droplets to be added later. In particular, one or more reaction droplets may be manipulate in the air gap (moved, mixed, heated, etc.) and temporarily or permanently moved out of the air gap and into a reaction chamber well though a reaction chamber opening. As shown, some of the reaction chamber openings 105' pass through an actuation electrode. As will be shown in greater detail herein, the reaction chamber may itself include additional actuation electrodes that may be used to move a reaction chamber droplet into/out of the reaction chamber well. In some variations one or more actuation electrodes may be continued (out of the plane of the air gap) into the reaction chamber well.

In general, one or more additional reagents may be subsequently introduced either manually or by automated means in the air gap. In some instances, the access holes may be actual access ports that may couple to outside reservoirs of reagents or reaction components through tubing for introducing additional reaction components or reagents at a later time. As mentioned, the access holes (including reaction chamber openings) may be located in close proximity to a DMF actuation electrode(s). Access holes 105, 105' may also be disposed on the side or the bottom of the DMF apparatus. In general, the apparatus may include a controller 110 for controlling operation of the actuation electrodes, including moving droplets into and/or out of reaction chambers. The controller may be in electrical communication with the electrodes and it may apply power in a controlled manner to coordinate movement of droplets within the air gap and into/out of the reaction chambers. The controller may also be electrically connected to the one or more temperature regulators (thermal regulators 120) to regulate temperature in the thermal zones 115. One or more sensors (e.g., video sensors, electrical sensors, temperature sensors, etc.) may also be included (not shown) and may provide input to the controller which may use the input from these one or more sensors to control motion and temperature.

Figures 2A, 2B, 2C, 2D:
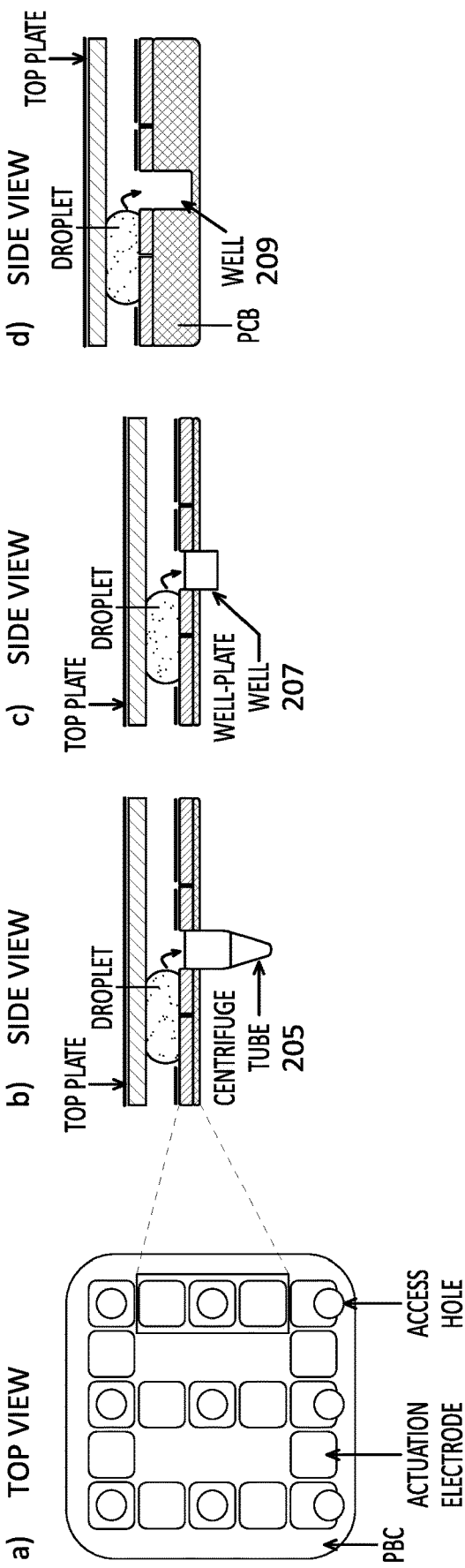
FIG. 2A shows the top view of FIG. 1 and FIGS. 2B-2D show side views of variations of reaction chamber wells that may be used in an air-matrix DMF apparatus.
In FIG. 2B the reaction chamber well comprises a centrifuge tube.
in FIG. 2C the reaction chamber well comprises a well plate (which may be part of a multi-well plate); and in FIG. 2D the reaction chamber well is formed as part of the pate of the air-matrix DMF apparatus.

As indicated above, surface fouling is an issue that has plagued microfluidics, including DMF devices. Surface fouling occurs when certain constituents of a reaction mixture irreversibly adsorbs onto a surface that the reaction mixture is in contact with. Surface fouling also appears more prevalent in samples containing proteins and other biological molecules. Increases in temperature may also contribute to surface fouling. The DMF apparatuses and methods described herein aim to minimize the effects of surface fouling. One such way is to perform the bulk of the reaction steps in a reaction chamber that is in fluid communication with the air gap layer. The reaction chamber may be an insert that fits into an aperture of the DMF device as shown in FIGS. 2B and 2C. FIG. 2B shows the floor (e.g., first plate) of an air gap region coupled to a centrifuge (e.g., Eppendorf) tube 205 while FIG. 2C incorporates a well-plate 207 (e.g., of a single or multi-well plate) into the floor of the air gap region. A built-in well 209 may also be specifically fabricated to be included in the air-matrix DMF apparatus as shown in FIG. 2D. When a separate or separable tube or plate is used, the tubes may be coupled to the DMF device using any suitable coupling or bonding means (e.g. snap-fit, friction fit, threading, adhesive such as glue, resin, etc., or the like).

In general, having a dedicated reaction chamber within the DMF device minimizes surface fouling especially when the reaction is heated. Thus, while surface fouling may still occur within the reaction chamber, it may be mainly constrained to within the reaction chamber. This allows the majority of the air gap region floor to remain minimally contaminated by surface fouling and clear for use in subsequent transfer of reagents or additional reaction materials if needed, thus allowing for multi-step or more complex reactions to be performed. When the reaction step or in some instances, the entire reaction is completed, the droplet containing the product may be moved out of the reaction chamber to be analyzed. In some examples, the product droplet may be analyzed directly within the reaction chamber.

Figure 3A:
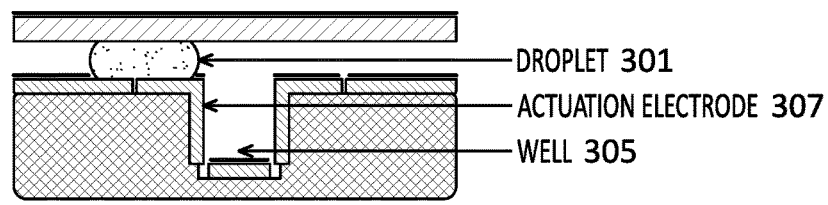
FIGS. 3A-3E illustrate movement (e.g., controlled by a controller of an air-matrix DMF apparatus) into an then out of a reaction chamber, as described herein. In this example, the reaction chamber well is shown in a side view of the air-matrix DMF apparatus and the reaction chamber is integrally formed into a plate (e.g., a first or lower plate) of the air-matrix DMF apparatus which includes actuation electrodes (reaction well actuation electrodes) therein.
Figure 3B:
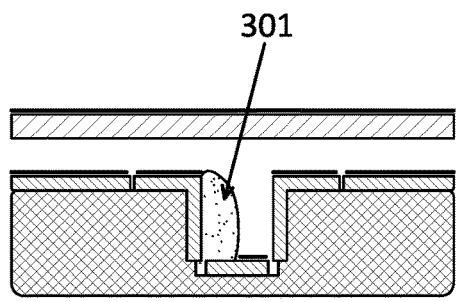
Figure 3C:
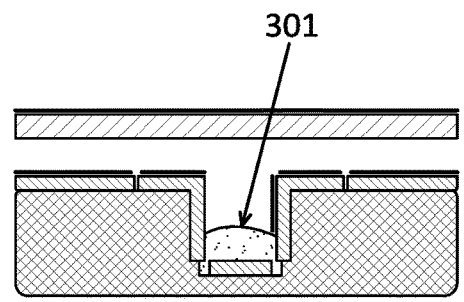

In order to bring the droplet(s) containing the starting materials and the reagent droplets into the reaction chamber, additional actuation electrodes, which may also be covered/coated with a dielectric and a hydrophobic layer (or a combined hydrophobic/dielectric layer), may be used. FIGS. 3A-3E show a series of drawings depicting droplet 301 movement into and out of an integrated well 305. As this series of drawings show, in addition to lining the floor of the air gap layer, additional actuation electrodes 307 line the sides and the bottom of the well. In some variations, the same actuation electrode in the air gap may be extended into the reaction chamber opening. The actuation electrodes 307 (e.g., the reaction chamber actuation electrodes) may be embedded into or present on the sides and bottom of the well for driving the movement of the droplets into/out of the reaction chamber well. Actuation electrodes may also cover the opening of the reaction chamber. In FIG. 3A, a droplet 301 (e.g., reaction droplet) in the air gap layer may be moved (using DMF) to the reaction chamber opening. The actuation electrodes 307 along the edge of the well and the sides of the well maintain contact with the droplet as it moved down the well walls to the bottom of the well (shown in FIGS. 3B and 3C). Once in the reaction chamber well, the droplet may be covered (as described in more detail below, either by placing a cover (e.g., lid, cap, etc.) over the reaction chamber opening and/or by mixing the droplet with a covering (e.g., encapsulating) material such as an oil or wax (e.g., when the droplet is aqueous). In general, the droplet may be allowed to react further within the well, and may be temperature-regulated (e.g., heated, cooled, etc.), additional material may be added (not shown) and/or it may be observed (to detect reaction product). Alternatively or additionally, the droplet may be moved out of the well using the actuation electrodes; if a mechanical cover (e.g., lid) has been used, it may be removed first. If an encapsulating material has been used it may be left on.

In some variations contacts may penetrate the surfaces of the reaction chamber. For example, there may be at least ten electrical insertion points in order to provide sufficient electrical contact between the actuation electrodes and the interior of the reaction chamber. In other examples there may need to be at least 20, 30, or even 40 electrical insertion points to provide sufficient contact for all the interior surfaces of the reaction chamber. The interior of the reaction chamber may be hydrophobic or hydrophilic (e.g., to assist in accepting the droplet). As mentioned, an electrode (actuation electrode) may apply a potential to move the droplets into and/or out of the well.

Figure 3D:
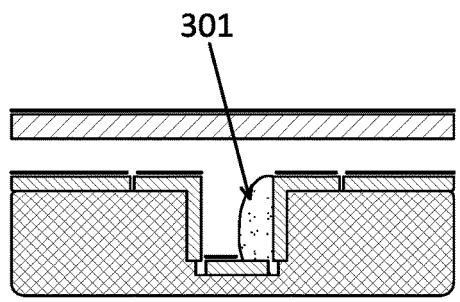
Figure 3E:
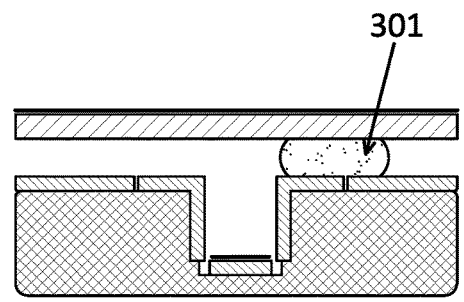

In general, the actuation electrodes may bring the droplet into the well in a controlled manner and minimizes dispersion of the droplet as it is moved into the well and thus maintaining as cohesive a sample droplet as possible. FIGS. 3D and 3E show the droplet being moved up the wall of the well and then out of the reaction chamber. This may be useful for performing additional subsequent steps or for detecting or analyzing the product of interest within the droplet, although these steps may also or alternatively be performed within the well. Actuation electrodes may be on the bottom surface, the sides and the lip of the well in contact with the air gap layer; some actuation electrodes may also or alternatively be present on the upper (top) layer.

In instances where the reaction compartment is an independent structure integrated with the DMF devices as those shown in FIGS. 2A and 2B, the thickness of the substrate (e.g. PCB) may be similar to what is commonly used in DMF fabrication. When the reaction compartment is an integrated well structure fabricated in the bottom plate of the DMF device as shown in FIG. 2D, the thickness of the substrate may be equivalent to the depth of the well.

In another embodiment, the electrodes embedded in the reaction compartments can include electrodes for the electrical detection of the reaction outputs. Electrical detection methods include but are not limited to electrochemistry. In some instances, using the changes in electrical properties of the electrodes when the electrodes contact the reaction droplet, reagent droplet, or additional reaction component to obtain information about the reaction (e.g., changes in resistance correlated with position of a droplet).

The apparatuses described herein may also prevent evaporation. Evaporation may result in concentrating the reaction mixture, which may be detrimental as a loss of reagents in the reaction mixture may alter the concentration of the reaction mixture and result in mismatched concentration between the intermediate reaction droplet with subsequent addition of other reaction materials of a given concentration. In some variations, such as with enzymatic reactions, enzymes are highly sensitive to changes in reaction environment and loss of reagent may alter the effectiveness of certain enzymes. Evaporation is especially problematic when the reaction mixture has to be heated to above ambient temperature for an extended period of time. In many instances, microfluidics and DMF devices utilizes an oil-matrix for performing biochemical type reactions in microfluidic and DMF devices to address unwanted evaporation. One major drawback of using an oil in the DMF reaction is the added complexity of incorporating additional structures to contain the oil.

The well or reaction chamber structure described herein provides a simple solution for maintaining oil in a DMF device. FIGS. 4A and 4B show the DMF devices having a well or tube integrated into its structure (reaction chamber well) where the well or tube may including a protective/coating material such as oil 405, 407. This may allow the reaction steps that require heating to be performed in an oil environment where the oil is able to limit evaporation of the reaction mixture. If additional steps are still required, the reaction droplet may be brought out of the tube or well through use of the actuation electrodes to move the reaction droplet to a different location. Other covers comprising coating or covering agents may include wax materials (e.g., paraffin, etc.) or the like, which may be melted to combine with and cover/coat the reaction droplet. The temperature may be adjusted to add (or in some variations, remove) the wax material from the droplet. As described in greater detail below, a wax material may be used in the air gap directly, without a dedicated reaction chamber (or forming the reaction 'chamber' in the air gap from the wax material).

Figure 5A:
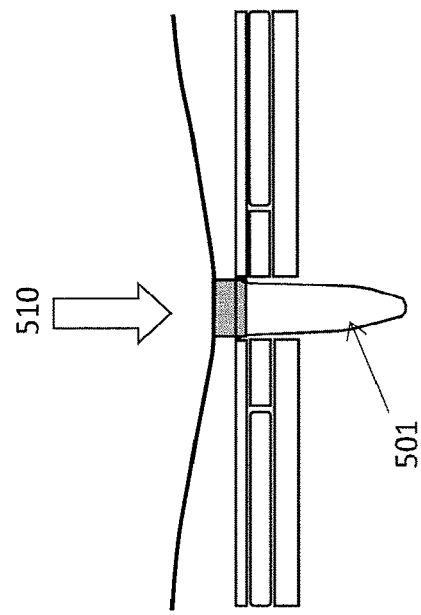
FIGS. 5A-5B show a side view of one example of a portion of an air-matrix DMF apparatus in which the top plate is flexible and includes a cover (e.g., plug, cap, lid, etc.) for the reaction chamber opening that is coupled to the plate.
Figure 5B:
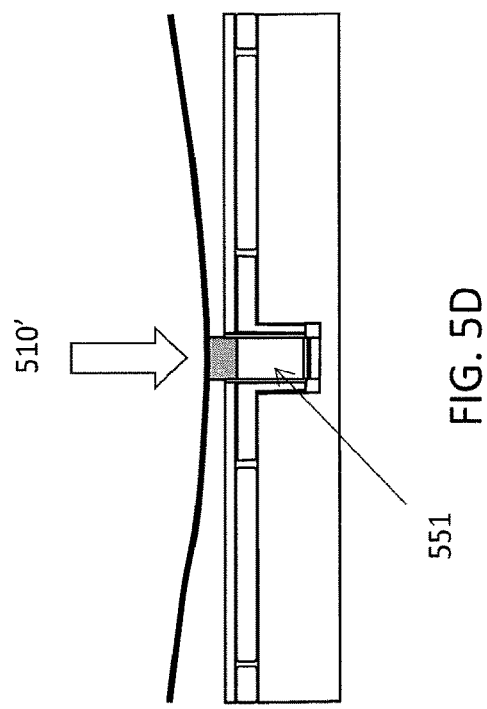
Figure 5C:
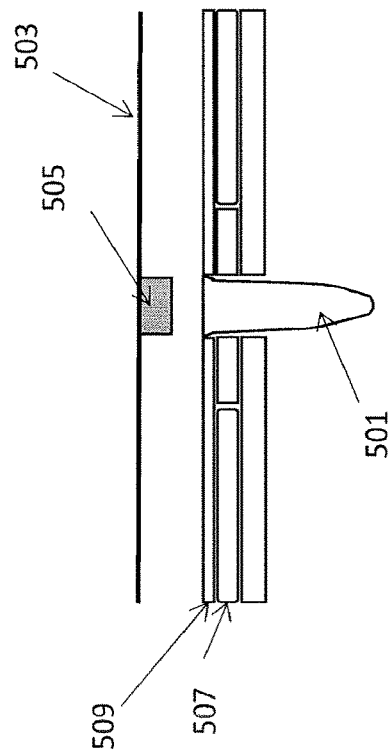
FIGS. 5C-5D illustrate sealing of another variation of a reaction chamber well using a flexible top plate having an integrated cover opposite from the reaction chamber well opening.

Covering the droplet may allow performance of reaction steps (particularly those that require heating) and may limit evaporation. For example, the reaction chamber well may be mechanically covered by covering the reaction chamber opening. FIGS. 5A-5C suggest one way of covering a reaction chamber opening using a cap, plug, or lid 505 that is coupled to the upper plate 503. In this example, the top plate of the DMF apparatus may be flexible. When force 510 is applied to an outer surface of the top plate, the plate becomes deformed and the cap 505 is pushed down into the reaction well opening, sealing the reaction chamber well 501, as shown in FIG. 5B. In the example of FIGS. 5A and 5B the reaction chamber well is a tube 505 (e.g., microfuge tube, etc.). The air-matrix DMF apparatus includes a lower plate with actuation electrodes 507 covered by a hydrophobic (and in this example, dielectric) layer 509.

Figure 5D:
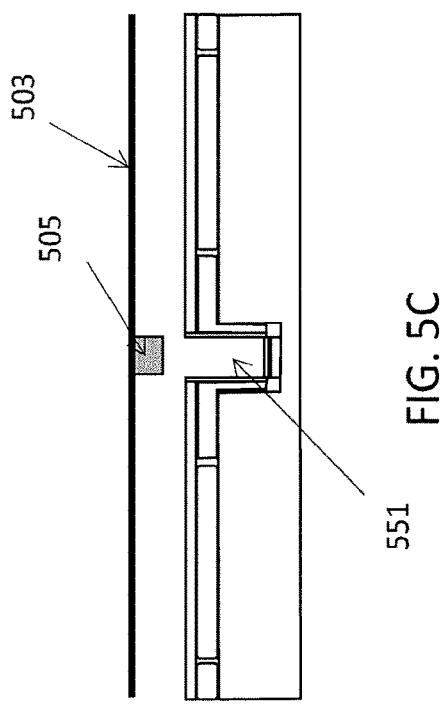

Similarly, FIGS. 5C and 5D illustrate a variation in which the reaction chamber/well 551 is formed into the lower plate and the upper plate 503 also includes a cover 505 (e.g., cap, lid, plug, etc.). Alternatively, the upper plate may be lowered over the cover to seal the reaction chamber/well opening even if it does not include a separate cover, etc. For example the upper plate itself may cover the opening. In general, it is not necessary that the upper plate be flexible, as the entire upper plate may be lowered to seal the reaction chamber well (not shown); the upper plate may later be restored to the same air gap width if desired, and the droplet may be returned to the air gap or not, as illustrated in FIGS. 3A-3E for additional processing/detection. Being able to perform a heated step of a reaction in a closed chamber may aid with evaporation prevention and, unlike instances where the entire DMF device is placed in a humidifying chamber, does not cause unwanted condensation in other regions of the DMF device.

Another method that has been developed to combat evaporation is the use of wax (e.g. paraffin) in minimizing evaporation during a reaction. A wax substance may include substances that are composed of long alkyl chains. Waxes typically solids at ambient temperatures having a melting point of approximately 46° C. to approximately 68° C. depending upon the amount of substitution within the hydrocarbon chain. In some instances higher melting point waxes may be purifying crude wax mixtures.

As mentioned above, the wax is one type of sealing material that may be used as a cover (e.g., within a reaction chamber that is separate from the plane of the air gap. In some variations, wax may be used within the air gap. In particular, the wax may be beneficially kept solid until it is desired to mix it with the reaction droplet so that it may coat and protect the reaction droplet. Typically the wax material (or other coating material) may be mixed with the reaction droplet and enclose (e.g., encapsulate, surround, etc.) the aqueous reaction droplet.

When a reaction droplet is maintained within a paraffin coating, not only is evaporation minimized, but the paraffin may also insulate the reaction droplet from other potentially reaction interfering factors. In some instances, a solid piece of paraffin or other wax substance may be placed within a thermal zone of the air gap layer of the DMF device. For example, during a reaction, actuation electrodes may move a reaction droplet to a wax (e.g., paraffin) body. Upon heating to a melting temperature, the wax body may melt and cover the reaction droplet. The reaction then may continue for an extended period of time (including at elevated temperatures) without need to replenish the reaction solvents, while preventing loss by evaporation. For example wax-encapsulated droplet may be held and/or moved to a thermal zone to control the temperature. The temperature may be decreased or increased (allowing control of the phase of the wax as well, as the wax is typically inert in the reactions being performed in the reaction droplet). The temperature at that particular thermal zone may be further increased to melt the paraffin and release the reaction droplet. The reaction droplet may be analyzed for the desired product when encapsulated by the liquid or solid wax, or it may be moved to another region of the DMF device for further reaction steps after removing it from the wax covering. Paraffins or other wax materials having the desired qualities (e.g. melting point above the reaction temperature) may be used. For example, paraffins typically have melting points between 50 and 70 degrees Celsius, but their melting points may be increased with increasing longer and heavier alkanes.

Figure 6A:
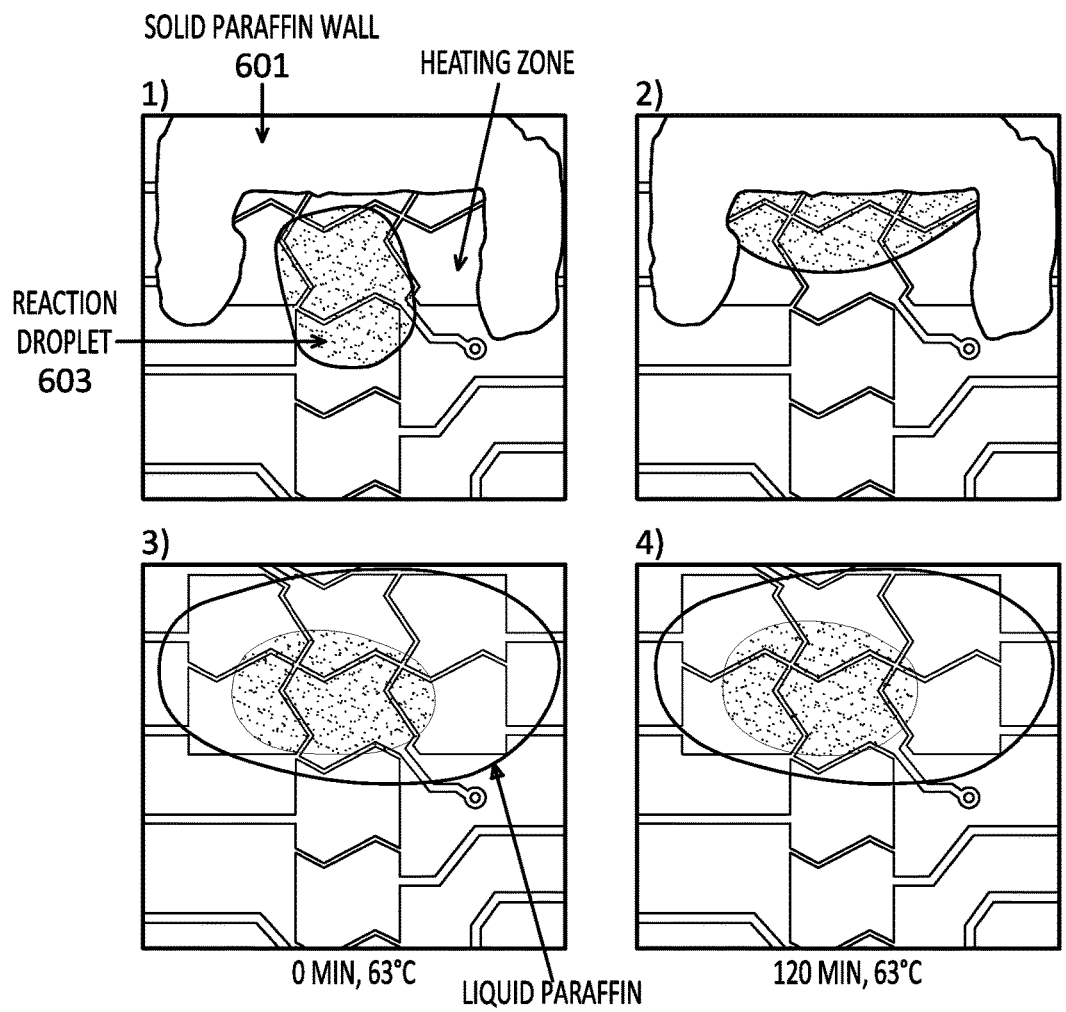
FIG. 6A shows a time series of photos of an air matrix DMF apparatus including a wax (in this example, paraffin) body which is melted and covers a reaction droplet.
Figure 6B:
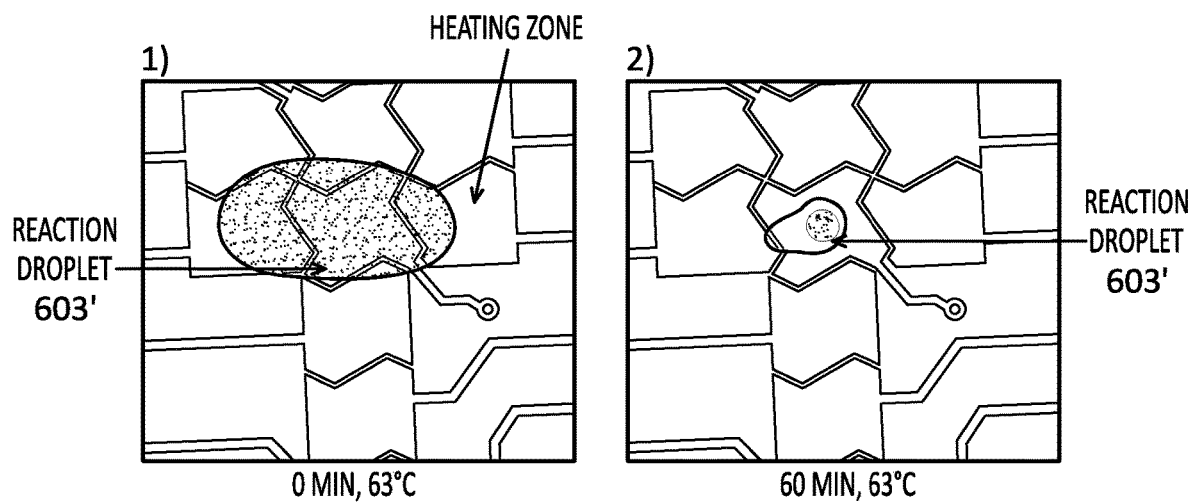
FIG. 6B is an example of a time series similar to that shown in FIGS. 6A(3) and 6A(4), without using a wax body to cover the reaction droplet, showing significant evaporation.

FIG. 6A shows time-sequence images (numbered 1-4) taken from an example using a wax body within the air matrix as discussed above, showing profound reduction in evaporation as compared to a control without wax (shown in FIG. 6B, images 1-2). In FIG. 6A, the first image, in the top right, shows an 8 µL reaction droplet 603 that has been moved by DMF in the air matrix apparatus to a thermal zone ("heating zone") containing a solid wax body (e.g., paraffin wall 601). Once in position, the reaction droplet may be merged with a solid paraffin wall (e.g., thermally printed onto DMF), as shown in image 2 of FIG. 6A, or the wax material may be melted first (not shown). In FIG. 6A image 3, the thermal zone is heated (63° C.) to or above the melting point of the wax material thereby melting the paraffin around the reaction droplet, and the reaction droplet is surrounded/encapsulated by the wax material, thus preventing the droplet from evaporation as shown in FIG. 6A images 3 and 4. Using this approach, in the example shown in FIG. 6A image 4, the volume of reaction droplets was maintained roughly constant at 63° C. for an incubation time approximately two hours long (120 min). An equivalent experiment without the paraffin wall was performed, and shown in FIG. 6B. The left picture (image 1) in FIG. 6B shows the reaction droplet 603' at time zero at 63° C. and the right picture of FIG. 6B shows the reaction droplet after 60 minutes at 63° C. As shown, the reaction droplet almost completely evaporated within approximately an hour's time at 63° C.

Through this approach of enclosing a droplet in a shell of liquid wax, the reaction volume and temperature are maintained constant without the use of oil, a humidified chamber, off-chip heating, or droplet replenishment methods. Waxes other than paraffin can be used to prevent droplet evaporation as long as their melting temperature is higher than the ambient temperature, but lower or equal to the reaction temperature. Examples of such waxes include paraffin, bees and palm waxes. The wax-like solids can be thermally printed on the DMF device surface by screen-, 2D- or 3D-printing. This wax-mediated evaporation prevention solution is an important advancement in developing air-matrix DMF devices for a wide variety of new high-impact applications.

As mentioned, the wax-based evaporation methods described may be used in conjunction with the DMF devices having a reaction chamber feature. In those instances, the wax may be present in the reaction chamber and the reaction droplet may be moved to the reaction chamber containing wax for performing the reaction steps requiring heating. Once the heating step has completed, the reaction droplet may be removed from the reaction chamber for detection or to perform subsequent reaction steps within the air gap layer of the DMF device.

The methods and apparatuses described herein may be used for preventing evaporation in air-matrix DMF devices and may enable facile and reliable execution of any chemistry protocols on DMF with the requirement for a temperature higher than the ambient temperature. Such protocols include, but are not limited to, DNA/RNA digestion/fragmentation, cDNA synthesis, PCR, RT-PCR, isothermal reactions (LAMP, rolling circle amplification-RCA, Strand Displacement Amplification-SDA, Helicase Dependent Amplification-HDA, Nicking Enzyme Amplification reaction-NEAR, Nucleic acid sequence-based amplification-NASBA, Single primer isothermal amplification-SPIA, cross-priming amplification-CPA, Polymerase Spiral Reaction-PSR, Rolling circle replication-RCR), as well as ligation-based detection and amplification techniques (ligase chain reaction-LCR, ligation combined with reverse transcription polymerase chain reaction-RT PCR, ligation-mediated polymerase chain reaction-LMPCR, polymerase chain reaction/ligation detection reaction-PCR/LDR, ligation-dependent polymerase chain reaction-LD-PCR, oligonucleotide ligation assay-OLA, ligation-during-amplification-LDA, ligation of padlock probes, open circle probes, and other circularizable probes, and iterative gap ligation-IGL, ligase chain reaction-LCR, over a range of temperatures (37-100° C.) and incubation times (≥2 hr).

Example 1: Device Fabrication and Assembly

DMF apparatuses that include embedded centrifuge tubes and/or well-plate wells (e.g., FIGS. 2B, 2C) were constructed by drilling 5.5 mm diameter holes into 3 mm thick PCB substrates, bearing copper (43 µm thick) plated with nickel (185 µm) and gold (3.6 µm) for electrodes and conductive traces. Tubes and wells were then inserted into holes. DMF devices with embedded wells (e.g., FIG. 2D) were fabricated with holes (5 mm diameter, 10 mm depth) drilled in 15 mm thick PCB substrates. Actuation electrodes (each 10 mm×10 mm) were formed by conventional photolithography and etching, and were coated with soldermask (~15 µm) as the dielectric. As shown in FIGS. 3A-3E, some of the electrodes were formed around and adjacent to the hole which served as the access point to reaction compartments. The electrical contact pads were masked with polyimide tape (DuPont; Hayward, CA), and the substrate was spin-coated with a 50 nm layer of Teflon-AF (1% wt/wt in Fluorinert FC-40, 1500 rpm for 30 sec) and then baked at 100° C. for 3 h. The top plate of the DMF device, consisting of a glass substrate coated uniformly with unpatterned indium tin oxide (ITO) (Delta Technologies Ltd; Stillwater, MN) with 5.5 mm diameter PDMS plugs was spin-coated with 50 nm of Teflon-AF, as described above.

Prototype devices fabricated as described above performed better or as well as air-gap DMF apparatuses without reaction chambers.

Example 2: Quantifying Evaporation Prevention Using Waxes

Figure 7:
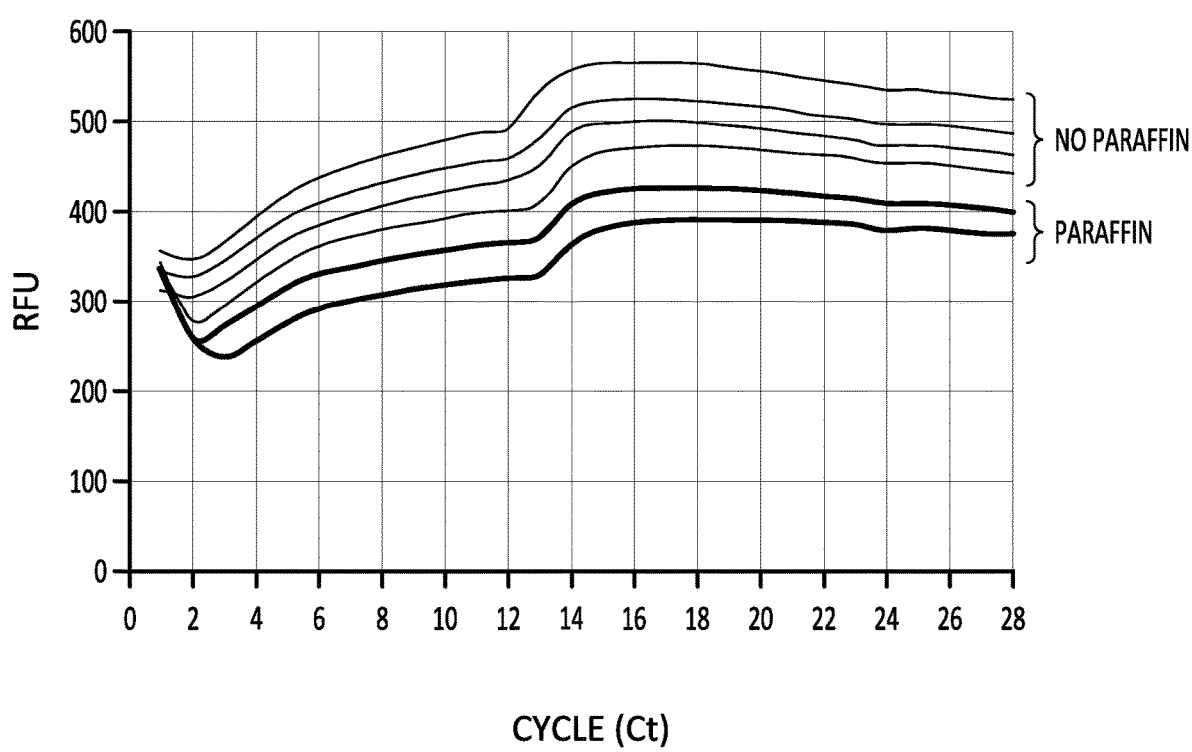
FIG. 7 is a graph comparing an amplification reaction by LAMP with and without a wax covering as described herein, protecting the reaction droplet from evaporation.
Figure 8A:
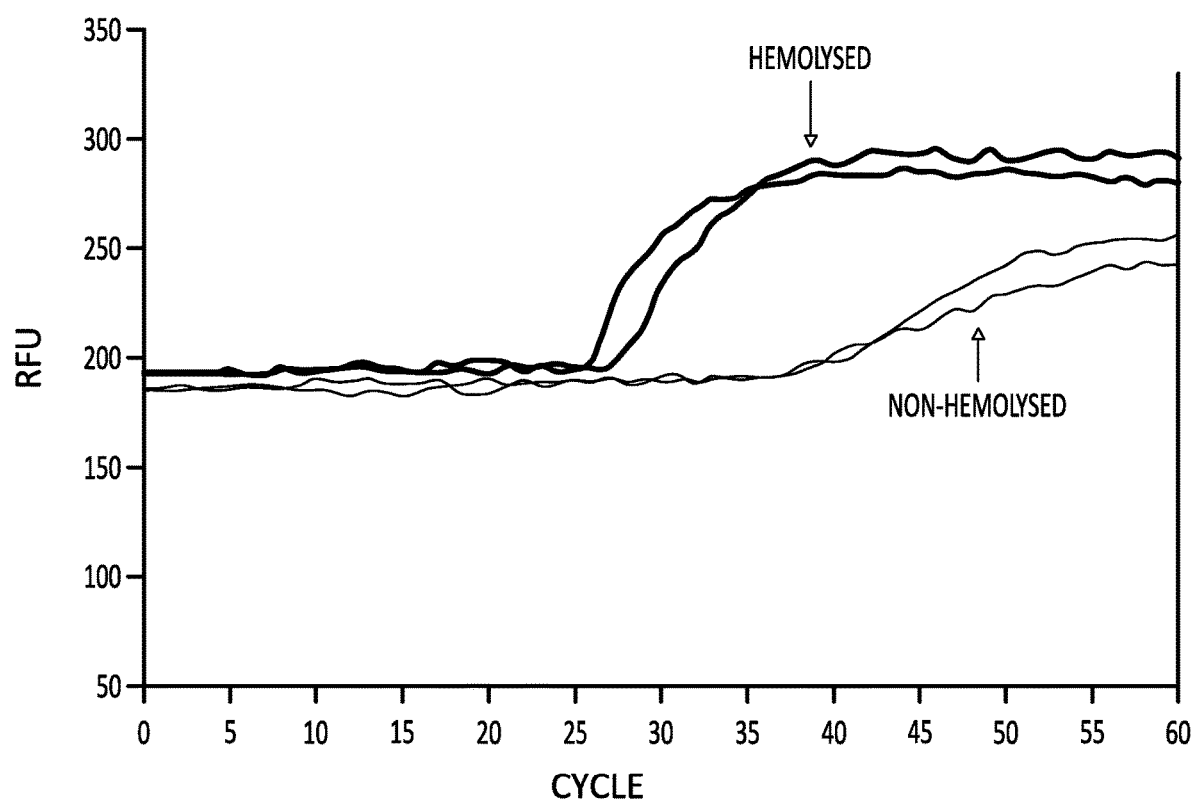
FIG. 8A show graphical results of LAMP using paraffin-mediated methods; this may be qualitatively compared to the graph of FIG. 8B shows graphical results of LAMP using conventional methods.
Figure 8B:
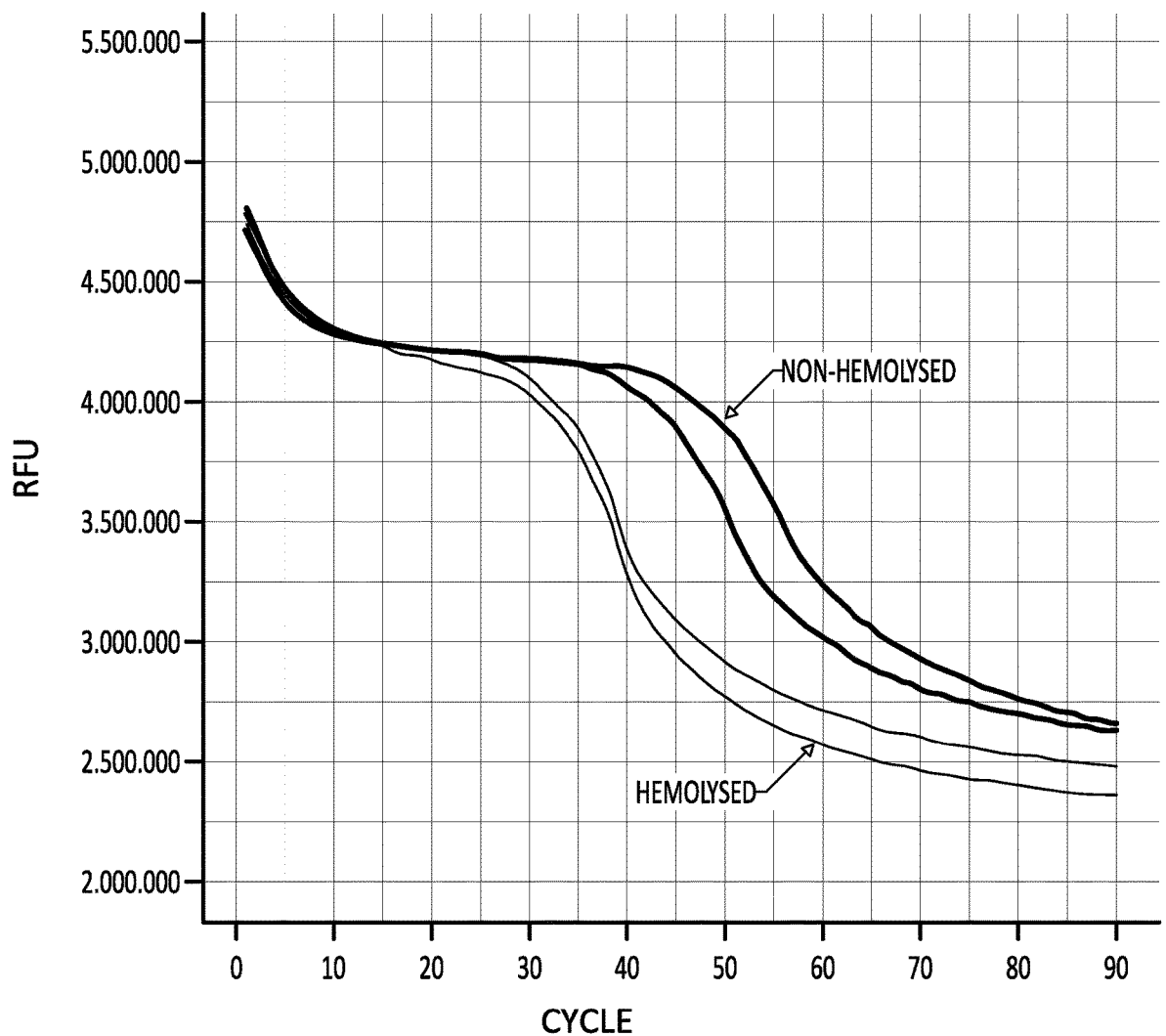

To qualitatively evaluate the effect of wax bodies to prevent evaporation in our assays, loop mediated amplification (LAMP) reactions were executed while covered in liquid paraffin wax in tubes on the benchtop using a real-time PCR Machine. As shown in FIG. 7, the LAMP assay amplified miR-451, and the $C_t$ values with and without paraffin were comparable (~13 cycles), indicating no significant effect on the assay. For LAMP on DMF, the reaction droplet (8 µL) was driven to heating zone (as shown in FIG. 6A). There, the droplet wets the solid paraffin wax wall which under conditional heating at 63° C. will melt into liquid wax to encircle the reaction volume and maintain it intact throughout the incubation time at 63° C. FIG. 8A shows a LAMP assay using paraffin-mediated methods, while FIG. 8B shows a LAMP assay using conventional methods. In FIG. 8A, the two upper traces are for a hemolyzed sampled while the two lower traces are for a non-hemolyzed sample. The two traces of each are to show repeatability of the runs using wax-mediated air matrix DMF. In FIG. 8B, the conventional LAMP assay for a hemolyzed sample are shown in upper two traces while the non-hemolyzed LAMP runs are shown in lower two traces. Again, the two upper and two lower traces each are to show result repeatability. The wax-mediated approach on DMF generated results comparable in $C_t$ values to those generated by conventional LAMP in tubes as shown in FIGS. 8A and 8B.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of operating a microfluidic apparatus, the method comprising:
    dispensing a reaction droplet within an air gap of the microfluidic apparatus having a bottom surface that is open to air above the bottom surface;
    moving the reaction droplet to a region of the microfluidic apparatus having a wax material; and
    surrounding the reaction droplet with the wax material; and
    moving the surrounded reaction droplet within the air gap.

2. The method of claim 1, wherein the moving the reaction droplet includes moving the reaction droplet to a heating zone including the wax material.

3. The method of claim 2, further comprising modifying a temperature of the heating zone after surrounding the reaction droplet with the wax material.

4. The method of claim 1, wherein the wax material prevents the reaction droplet from evaporation.

5. The method of claim 1, wherein the wax material has a melting temperature higher than an ambient temperature and lower than a reaction temperature.

6. The method of claim 1, wherein the wax material is thermally printed onto the bottom surface.

7. The method of claim 1, wherein moving the reaction droplet includes applying energy to a subset of electrodes of the microfluidic apparatus.

8. The method of claim 7, wherein the subset of electrodes are disposed adjacent to the bottom surface.

9. The method of claim 1, wherein moving the reaction droplet includes moving the reaction droplet into a wall formed from the wax material.

10. The method of claim 1, further comprising moving the reaction droplet out from the wax material.

11. A method of operating a microfluidic apparatus, the method comprising:

dispensing a reaction droplet within an air gap of the microfluidic apparatus having a bottom plate that is open to air above the bottom plate;
melting a wax material disposed at a thermally controlled region of the microfluidic apparatus; and
moving the reaction droplet into the melted wax material, wherein the melted wax material encapsulates the reaction droplet.

12. The method of claim 11, wherein moving the reaction droplet includes applying energy to a subset of electrodes adjacent to the bottom plate.

13. The method of claim 11, wherein the wax material has a melting temperature higher than an ambient temperature and lower than a reaction temperature.

14. The method of claim 11, wherein the wax material is screened onto the bottom plate prior to melting.

15. The method of claim 11, wherein the melted wax material prevents the reaction droplet from evaporation.

16. The method of claim 11, further comprising moving the reaction droplet out of the melted wax material.

17. The method of claim 11, further comprising, holding the thermally controlled region at a temperature sufficient to maintain the wax material in a liquid state.

18. The method of claim 11, further comprising moving additional reaction components into the melted wax material after the reaction droplet has been moved into the melted wax material.

19. The method of claim 11, further comprising modifying a temperature of the thermally controlled region after moving the reaction droplet into the melted wax material.

20. The method of claim 19, further comprising decreasing the temperature of the thermally controlled region to solidify the wax material.

* * * * *